US009676796B2

(12) United States Patent
Kim et al.

(10) Patent No.: US 9,676,796 B2
(45) Date of Patent: Jun. 13, 2017

(54) TRICYCLIC BENZOXABOROLE COMPOUND, PREPARATION METHOD AND USE THEREOF

(71) Applicant: DONG-A ST CO., LTD., Seoul (KR)

(72) Inventors: Soon-Hoe Kim, Gyeonggi-do (KR); Weon-Bin Im, Gyeonggi-do (KR); Seung-Bum Ha, Seoul (KR); Jung-Sang Park, Gyeonggi-do (KR); Mi-Yeon Kim, Gyeonggi-do (KR); Sung-Hak Choi, Gyeonggi-do (KR); Hyun-Jung Sung, Gyeonggi-do (KR)

(73) Assignee: DONG-A ST CO., LTD. (KR)

( * ) Notice: Subject to any disclaimer, the term of this patent is extended or adjusted under 35 U.S.C. 154(b) by 0 days.

(21) Appl. No.: 14/908,006

(22) PCT Filed: Jul. 28, 2014

(86) PCT No.: PCT/KR2014/006894
§ 371 (c)(1),
(2) Date: Jan. 27, 2016

(87) PCT Pub. No.: WO2015/016558
PCT Pub. Date: Feb. 5, 2015

(65) Prior Publication Data
US 2016/0168167 A1    Jun. 16, 2016

(30) Foreign Application Priority Data

Jul. 30, 2013   (KR) .......................... 10-2013-0090493
Jul. 24, 2014   (KR) .......................... 10-2014-0093765

(51) Int. Cl.
*A61K 31/69*     (2006.01)
*C07F 5/02*      (2006.01)

(52) U.S. Cl.
CPC .............. *C07F 5/025* (2013.01); *A61K 31/69* (2013.01)

(58) Field of Classification Search
CPC ............................. A61K 31/69; C07F 5/025
See application file for complete search history.

(56) References Cited

U.S. PATENT DOCUMENTS

| 2005/0070503 | A1 | 3/2005 | Lee et al. |
| 2006/0234981 | A1 | 10/2006 | Baker et al. |
| 2007/0155699 | A1 | 7/2007 | Baker et al. |
| 2013/0165411 | A1 | 6/2013 | Gordeev et al. |
| 2015/0133402 | A1 | 5/2015 | Baker et al. |
| 2015/0215885 | A1 | 7/2015 | Park et al. |
| 2015/0216885 | A1 | 8/2015 | Baker et al. |

FOREIGN PATENT DOCUMENTS

| CN | 101420854 | A | | 4/2009 | |
| CN | 101772302 | A | | 7/2010 | |
| JP | 2009531292 | A | | 9/2009 | |
| JP | 2010530881 | A | | 9/2010 | |
| JP | 2013523826 | A | | 6/2013 | |
| KR | 20080110751 | A | | 12/2008 | |
| KR | 20100051615 | A | | 5/2010 | |
| RU | 2397986 | C2 | | 8/2010 | |
| WO | 2007095638 | A2 | | 8/2007 | |
| WO | 2008157726 | A1 | | 12/2008 | |
| WO | WO 2008157726 | A1 | * | 12/2008 | .............. C07F 5/025 |
| WO | 2009140309 | A2 | | 11/2009 | |
| WO | 2011060196 | A1 | | 5/2011 | |
| WO | 2011127143 | A1 | | 10/2011 | |
| WO | 2012033858 | A2 | | 3/2012 | |
| WO | 2013093615 | A1 | | 6/2013 | |
| WO | 2015021396 | A2 | | 2/2015 | |

OTHER PUBLICATIONS

Vincent Hernandez et al., 'Discovery of a Novel Class of Boron-Based Antibacterials with Activity against Gram-Negative Bacteria, Antimicrobial Agents and Chemotherapy, Mar. 2013, vol. 57, No. 3, p. 1394-1403.
International Search Report for Application No. PCT/KR2014/006894 dated Oct. 22, 2014.
Sunghak Choi, et al., Activity of Tedizolid Phosphate (TR-701) in Murine Models of Infection with Penicillin-Resistant and Penicillin-Sensitive *Streptococcus pneumoniae*, Antimicrobial Agents and Chemotherapy, Vo. 56, No. 9, Sep. 2012, pp. 4713-4717.
Extended European Search for EP Application No. 14831789.4 dated Mar. 3, 2017.

* cited by examiner

*Primary Examiner* — Jeffrey S Lundgren
*Assistant Examiner* — Ibrahim D Bori
(74) *Attorney, Agent, or Firm* — Lerner, David, Littenberg, Krumholz & Mentlik, LLP

(57) ABSTRACT

The present invention relates to a novel tricyclic benzoxaborole derivative, a preparation method thereof, and use of antibiotics pharmaceutical composition including the same as an active ingredient.

16 Claims, No Drawings

TRICYCLIC BENZOXABOROLE COMPOUND, PREPARATION METHOD AND USE THEREOF

CROSS-REFERENCE TO RELATED APPLICATION

This application is a national phase entry under 35 U.S.C. §371 of International Application No. PCT/KR2014/006894, filed Jul. 28, 2014, which claims priority to Korean Patent Application No. 10-2013-0090493, filed Jul. 30, 2013 and Korean Patent Application No. 10-2014-0093765, filed Jul. 24, 2014, the disclosures of which are incorporated herein by reference.

TECHNICAL FIELD

The present invention relates to a novel tricyclic benzoxaborole derivative, a preparation method thereof, and use of antibiotics including the same as an active ingredient, and preferably, to use of antibiotics against Gram-negative bacterium.

RELATED ART

Therapeutic agents for Gram-negative bacteria had been actively developed during the 1960s to 1980s. However, Gram-negative bacteria have not been studied since the 1990s, because interest in Gram-positive bacteria has been increased due to social issues of methicillin-resistant *Staphylococcus aureus* (MRSA) infection. Since the late 2000s, there have been increasing warnings about the lack of therapeutic agents for multidrug-resistant Gram-negative bacteria, and thus, they are recently receiving huge attention again.

At present, there are many drugs used for the treatment of Gram-negative bacterial infections, but they are not effective against multidrug-resistant Gram-negative bacteria. Due to growing demand for drugs that are effective against Gram-negative bacteria including multidrug-resistant Gram-negative bacteria, many pharmaceutical companies pay attention thereto, but not many antibiotics are under development. Further, the number of untreatable strains resistant to the known antibiotics is increasing, lead to serious social issues. Accordingly, there is a need for the development of new broad-spectrum antibiotics.

In protein synthesis of bacteria, an amino acid is activated by ATP to form aminoacyl-AMP, which binds to aminoacyl t-RNA synthetase, and the amino acid is transferred to t-RNA. Thus, t-RNA charging occurs, and at this time, the enzyme aminoacyl t-RNA synthetase can be a target of antibiotics.

In 2010, a new OBORT (Oxaborole t-RNA trapping) mechanism for Leucyl t-RNA synthetase was reported. This is a novel mechanism, regarding that an oxaborole compound binds to an editing domain of Leucyl t-RNA synthetase and binds to t-RNA terminal A76 via a covalent bond for t-RNA trapping. There is selectivity because of a structural difference between eukaryotic and bacterial editing domains. Therefore, a Leucyl t-RNA synthetase inhibitor can be developed as a drug effective against Gram-negative bacteria.

A benzoxaborole compound is not fermentation product, but a new synthetic antibiotic, and its derivatives having various structures are known. Boron-containing compounds such as oxaborole are described as useful antibiotic substances in US2006/0234981 and US2007/0155699. Further, the benzoxaborole derivatives are described in WO 2008/157726, WO2009/140309, WO2011/060196 and WO 2012/033858 and WO2013/093615.

WO2008/157726 specifically mentions only a derivative (Compound A) having no substituents at positions 7,8 of tricyclic benzoxaborole, for example, (7,8-dihydro-2H-1,6,9-trioxa-9a-borabenzo[cd]azulen-2-yl) methanamine. This tricyclic benzoxaborole compound exhibits a weak antibacterial activity against plurality of Gram-negative bacteria, and also little antibacterial activity against *Acinetobacter baumannii*, in particular, carbapenem-resistant *Acinetobacter baumannii*.

WO2013/093615 discloses only specific synthesis examples of a compound having a substituent at position 8 and a compound substituted with a hydroxymethyl group at position 7 of tricyclic benzoxaborole.

Accordingly, there is an urgent need for a novel benzoxaborole compound which selectively binds to Gram-negative bacteria to show its functional activity and minimizes side effects, and a therapeutic agent including the same for the treatment of Gram-negative bacterial infections, in particular, multidrug-resistant Gram-negative bacteria which have emerged as a serious threat.

DISCLOSURE

Technical Problem

An object of the present invention is to provide a novel tricyclic benzoxaborole compound.

Another object of the present invention is to provide a preparation method of the novel tricyclic benzoxaborole compound.

Still another object of the present invention is to provide an antibiotic against Gram-negative bacteria including multidrug-resistant Gram-negative bacteria, in which the antibiotic includes the novel tricyclic benzoxaborole compound as an active ingredient. The compound of the present invention selectively binds to Gram-negative bacteria to show its functional activity, thereby minimizing side effects. The additional object of the present invention is to provide an antibacterial, sterilizing or germicidal method for Gram-negative bacteria using the tricyclic benzoxaborole compound according to the present invention.

The additional object of the present invention is to provide a method for preventing or treating Gram-negative bacterial infections, including the step of administering to a subject a therapeutically effective amount of the tricyclic benzoxaborole compound according to the present invention.

Still another object of the present invention is to provide antibacterial, sterilizing or germicidal use of the tricyclic benzoxaborole compound according to the present invention against Gram-negative bacteria.

The additional object of the present invention is to provide use of the tricyclic benzoxaborole compound according to the present invention in the prevention or treatment of Gram-negative bacterial infections.

Technical Solution

The present invention provides a tricyclic benzoxaborole compound represented by the following Chemical Formula 1, an isomer thereof, or a pharmaceutically acceptable salt thereof.

[Chemical Formula 1]

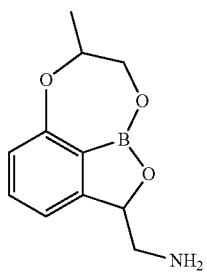

In another embodiment, the present invention provides an antibiotic pharmaceutical composition against Gram-negative bacteria, including the compound of Chemical Formula 1, the isomer thereof, or the pharmaceutically acceptable salt thereof as an active ingredient. Preferably, the Gram-negative bacteria may be *Acinetobacter baumannii, Citrobacter freundii, Escherichia coli, Enterobacter cloacae, Enterobacter aerogenes, Klebsiella pneumoniae, Klebsiella oxytoca, Morganella morganii, Pseudomonas aeruginosa Proteus vulgaris, Proteus mirabilis, Neisseria gonorrhoeae* or *Serratia marcescens*. The Gram-negative bacteria may be carbapenem-resistant Gram-negative bacteria.

The present inventors have studied benzoxaborole compounds having therapeutic effects on bacterial infections, and they have prepared a compound which has an antibacterial effect in vitro being equivalent to or higher than the known substances and has an excellent antibacterial effect against Gram-negative bacteria in vivo, and they also found that this compound can be more effectively used as a therapeutic agent for Gram-negative bacterial infections, thereby completing the present invention.

Specifically, compared to the known (8-methyl-7,8-dihydro-2H-1,6,9-trioxa-9a-borabenzo[cd]azulen-2-yl)methanamine hydrochloride, the compound of the present invention was found to exhibit a powerful antibacterial activity against plurality of Gram-negative bacteria, in particular, carbapenem-resistant *Acinetobacter baumannii* in vitro, and to exhibit excellent therapeutic effects on bacterial infections in an in vivo efficacy test model. Further, compared to the known ((2S,8R)-2-(aminomethyl)-7,8-dihydro-2H-1,6,9-trioxa-9a-borabenzo[cd]azulen-8-yl)methanol hydrochloride, the compound of the present invention was found to exhibit a strong in vitro antibacterial activity against major pathogenic bacteria including *Acinetobacter baumannii*, and to exhibit excellent therapeutic effects on bacterial infections in an in vivo efficacy test model.

Therefore, the present inventors intend to provide a novel benzoxaborole compound which selectively binds to Gram-negative bacteria to show its functional activity and minimizes side effects, and an antibiotic and/or a therapeutic agent including the same for the treatment of infections with Gram-negative bacteria including *Acinetobacter baumannii*.

The terms as used herein will be briefly explained below.

As used herein, the term "pharmaceutically acceptable salt" refers to a salt of a compound that does not cause significant irritation to an organism to which the compound is administered, and does not abrogate the biological activity and properties of the compound, and in the present invention, it collectively refers to any salt that retains the biological effectiveness and properties of the compound of Chemical Formula 1 and is preferred in terms of pharmaceutical, biological, or other properties. The pharmaceutically acceptable salt may include acid addition salts formed by acids capable of forming a non-toxic acid addition salt containing pharmaceutically acceptable anions, for example, inorganic acids such as hydrochloric acid, sulfuric acid, nitric acid, phosphoric acid, hydrobromic acid, hydroiodic acid, etc.; organic carbonic acids such as tartaric acid, formic acid, citric acid, acetic acid, trichloroacetic acid, trifluoroacetic acid, gluconic acid, benzoic acid, lactic acid, mandelic acid, fumaric acid, maleic acid, salicylic acid, etc.; or sulfonic acids such as methanesulfonic acid, ethanesulfonic acid, benzenesulfonic acid, p-toluenesulfonic acid, etc. As a specific example thereof, an acid addition salt of the compound of one embodiment may be prepared by reacting free base forms of these compounds with a stoichiometric amount of the appropriate acid.

At this time, the reaction may be performed in water, an organic solvent or a mixture thereof, and specifically, in a non-aqueous medium such as ether, ethyl acetate, ethanol, isopropanol, acetonitrile, etc. In addition, according to the form of the pharmaceutically acceptable salt, each form of the salts can be obtained by a typical reaction which is apparent to those skilled in the art. Further, the pharmaceutically acceptable salt may be alkaline metal salts or alkaline earth metal salts formed by lithium, sodium, potassium, calcium, magnesium, etc., amino acid salts such as lysine, arginine, guanidine, etc., organic salts such as dicyclohexylamine, N-methyl-D-glucamine, tris (hydroxymethyl)methylamine, diethanolamine, choline, triethylamine, etc.

As used herein, the term "isomer" means a compound or a salt thereof that has the same chemical formula or molecular formula, but is optically or geometrically different. The isomer, salt thereof, and mixture thereof (racemic mixture) are also included in the scope of the present invention.

The tricyclic benzoxaborole compound according to the present invention may be a racemate of the compound, an enantiomer thereof, a diastereomer thereof, a mixture of enantiomers, or a mixture of diastereomers.

Specifically, the compound represented by Chemical Formula 1 may have an asymmetric carbon center. When the compound has an asymmetric carbon center, it may exist as an enantiomer thereof, a diastereomer thereof, or a racemate thereof. All types of isomers including the same may be also included in the scope of the compound according to one embodiment of the present invention.

The compound according to Chemical Formula 1 according to the present invention or the pharmaceutically acceptable salt thereof may exhibit polymorphism and exist in the form of solvate (e.g., hydrate, etc.). Further, individual compounds include stereoisomers thereof or mixtures thereof.

As used herein, the term "pharmaceutically effective amount" means an amount of the active ingredient that is enough to obtain a desired pharmaceutical effect, and according to circumstances, it means a concentration or administration dose of the active ingredient in the pharmaceutical composition, which is enough for the desired pharmaceutical effect.

Hereinafter, the present invention will be described in more detail.

In one embodiment of the present invention, a compound of the following Chemical Formula 1, an isomer thereof, or a pharmaceutically acceptable salt thereof is provided:

[Chemical Formula 1]

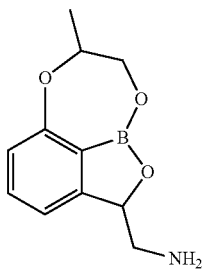

As used herein, the isomer means a compound or a salt thereof that has the same chemical formula or molecular formula, but is optically or geometrically different. The isomer, salt thereof, and mixture thereof (racemic mixture) are also included in the scope of the present invention.

Specifically, the isomer of the present invention or the tricyclic benzoxaborole compound may be a racemate of the compound, an enantiomer thereof, a diastereomer thereof, a mixture of enantiomers, or a mixture of diastereomers.

In one embodiment of the present invention, the isomer may be an enantiomer of the compound of Chemical Formula 1, a stereoisomer thereof, or a mixture of the isomers (racemic mixture). As the enantiomer, any asymmetric carbon atom on the compound may exist in any form of (R)-, (S)- and (R, S)-configurations, and preferably, in the separate form of (R)- or (S)-configuration.

At least one asymmetric carbon selected from the group consisting of carbons at positions 2 and 7 of the tricyclic benzoxaborole ring may be an enantiomer, for example, a (2S) isomer, a (2R) isomer, a (7S) isomer, a (7R) isomer, a (2S, 7S) isomer, a (2S, 7R) isomer, a (2R, 7S) isomer, or a (2R, 7R) isomer, but is not limited thereto.

In one specific embodiment of the present invention, the isomer of the present invention may be a (2S) isomer represented by the following Chemical Formula 2.

[Chemical Formula 2]

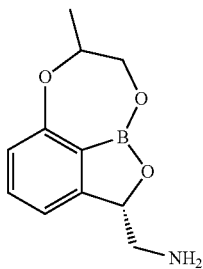

In another specific embodiment of the present invention, the isomer of the present invention may be a (2S, 7R) isomer represented by the following Chemical Formula 3.

[Chemical Formula 3]

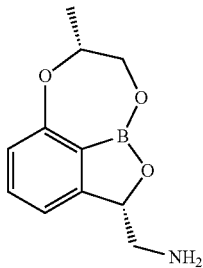

As an example according to the present invention, the compound of Chemical Formula 1 or the isomer thereof may be selected from the group consisting of the following compounds:

1) (7-methyl-7,8-dihydro-2H-1,6,9-trioxa-9a-borabenzo[cd]azulen-2-yl)methanamine hydrochloride;
2) ((2S)-7-methyl-7,8-dihydro-2H-1,6,9-trioxa-9a-borabenzo[cd]azulen-2-yl)methanamine hydrochloride;
3) ((2S,7R)-7-methyl-7,8-dihydro-2H-1,6,9-trioxa-9a-borabenzo[cd]azulen-2-yl)methanamine hydrochloride;
4) ((2S,7R)-7-methyl-7, 8-dihydro-2H-1,6,9-trioxa-9a-borabenzo[cd]azulen-2-yl) methanamine; and
5) ((2S,7S)-7-methyl-7,8-dihydro-2H-1,6,9-trioxa-9a-borabenzo[cd]azulen-2-yl)methanamine hydrochloride.

In one embodiment of the present invention, the tricyclic benzoxaborole compound of the present invention which is represented by Chemical Formula 1 may be used in the form of pharmaceutically acceptable salt. As the salt, an acid addition salt formed by a pharmaceutically acceptable free acid is useful. The free acid may be inorganic acids such as hydrochloric acid, sulfuric acid, nitric acid, phosphoric acid, hydrobromic acid, hydroiodic acid, etc.; organic carbonic acids such as tartaric acid, formic acid, citric acid, acetic acid, trichloroacetic acid, trifluoroacetic acid, gluconic acid, benzoic acid, lactic acid, mandelic acid, fumaric acid, maleic acid, salicylic acid, etc.; or sulfonic acids such as methanesulfonic acid, ethanesulfonic acid, benzenesulfonic acid, p-toluenesulfonic acid, etc., but is not limited thereto. For example, the tricyclic benzoxaborole compound of the present invention may be a pharmaceutically acceptable acid addition salt, hydrochloride.

Further, the tricyclic benzoxaborole compound of the present invention which is represented by Chemical Formula 1 may include all salts, hydrates, and solvates which can be prepared by the ordinary method, as well as pharmaceutically acceptable salt.

These pharmaceutically acceptable salts according to the present invention may be prepared by the ordinary method, and for example, by dissolving the compound of Chemical Formula 1 in a water-miscible organic solvent, e.g., acetone, methanol, ethanol, acetonitrile, etc., adding an excessive amount of an organic acid thereto, or by adding an acid aqueous solution of an inorganic acid thereto, and then precipitating or crystallizing it. Subsequently, a preparation may be performed by evaporating the solvent or an excessive amount of the acid from this mixture, and then drying it to obtain an addition salt or suction-filtrate a precipitated salt.

Further, the present invention provides a preparation method of the tricyclic benzoxaborole compound of Chemical Formula 1. The tricyclic oxaborole derivative of the present invention may be prepared by various methods according to the type of the stereoisomer, and by the method as illustrated below. It is apparent that the following preparation method is for illustrative purposes only, and it can be readily modified by those skilled in the art according to the desired compound. Therefore, the preparation method of the tricyclic benzoxaborole compound of the present invention is not intended to be limited by the following method.

The preparation method of the compound of Chemical Formula 1 according to the present invention may include the steps of:
coupling a compound of Chemical Formula 4 and a compound of Chemical Formula 5 to prepare a compound of Chemical Formula 6;

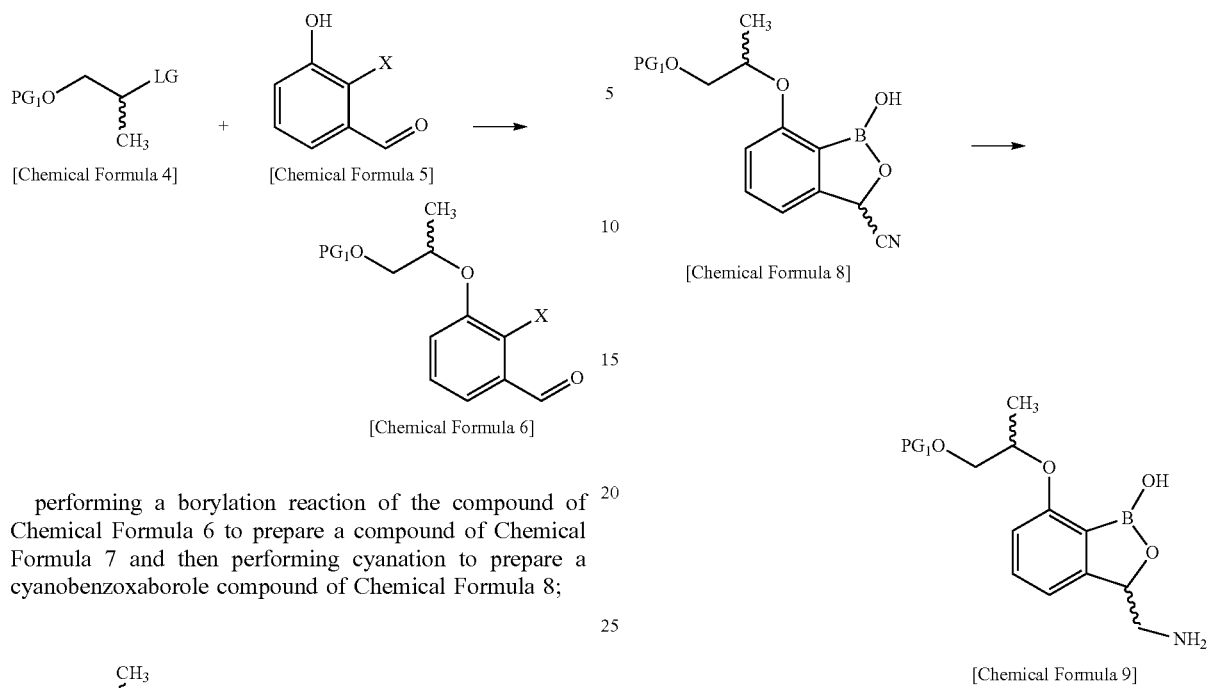

performing a borylation reaction of the compound of Chemical Formula 6 to prepare a compound of Chemical Formula 7 and then performing cyanation to prepare a cyanobenzoxaborole compound of Chemical Formula 8;

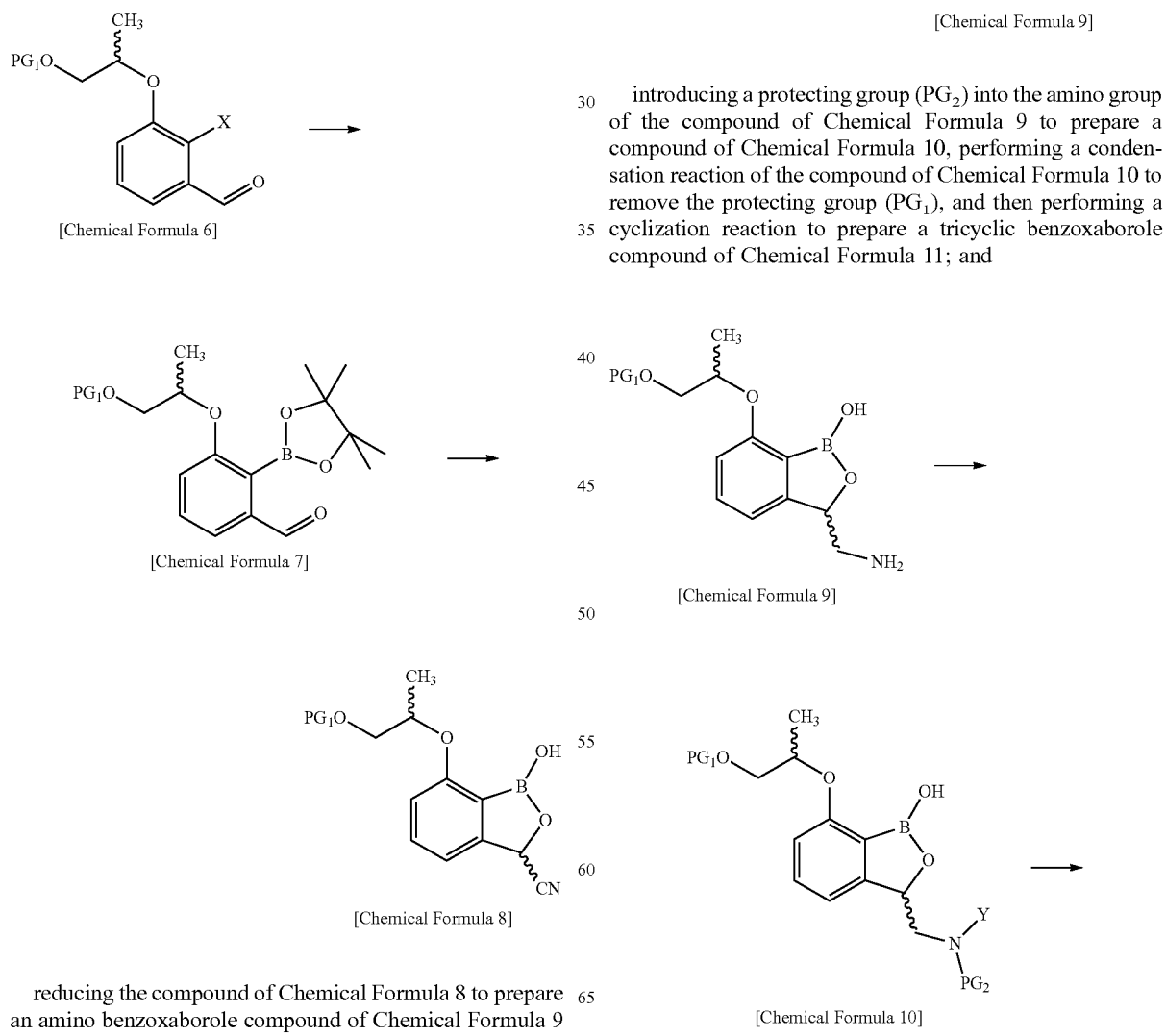

reducing the compound of Chemical Formula 8 to prepare an amino benzoxaborole compound of Chemical Formula 9 by substitution of the cyano group with an amino group;

introducing a protecting group (PG$_2$) into the amino group of the compound of Chemical Formula 9 to prepare a compound of Chemical Formula 10, performing a condensation reaction of the compound of Chemical Formula 10 to remove the protecting group (PG$_1$), and then performing a cyclization reaction to prepare a tricyclic benzoxaborole compound of Chemical Formula 11; and -continued

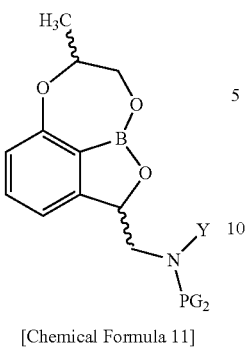

[Chemical Formula 11]

deprotecting the amino group (PG$_2$) of the compound of Chemical Formula 11 to prepare a compound of Chemical Formula 1.

Further, the preparation method of the compound of Chemical Formula 1 according to the present invention may include the steps of:

coupling the compound of Chemical Formula 4 and the compound of Chemical Formula 5 to prepare the compound of Chemical Formula 6;

[Chemical Formula 4]   [Chemical Formula 5]

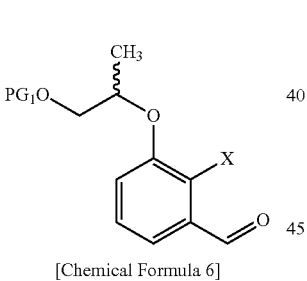

[Chemical Formula 6]

performing a nitration reaction of the compound of Chemical Formula 6 or using a chiral ligand or a chiral catalyst to prepare a compound of Chemical Formula 12 or isomers thereof, reducing the compound of Chemical Formula 12 to prepare the compound of Chemical Formula 13 by substitution of the nitro group with an amino group;

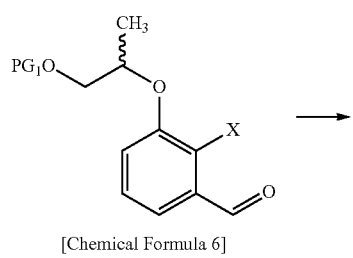

[Chemical Formula 6]

-continued

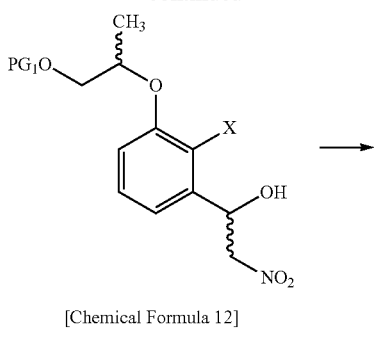

[Chemical Formula 12]

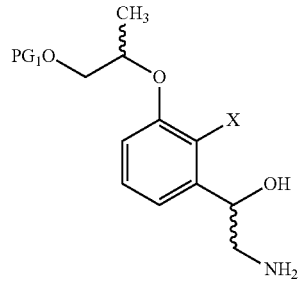

[Chemical Formula 13]

introducing a protecting group (PG$_2$) into the amino group of the compound of Chemical Formula 13 to prepare a compound of Chemical Formula 14, and performing a borylation reaction of the compound of Chemical Formula 14 to prepare the benzoxaborole compound of Chemical Formula 10; and

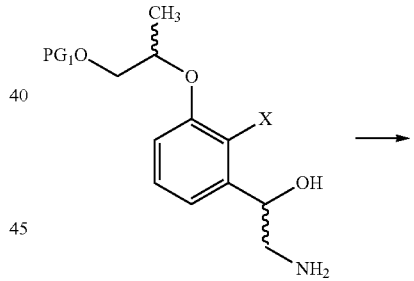

[Chemical Formula 13]

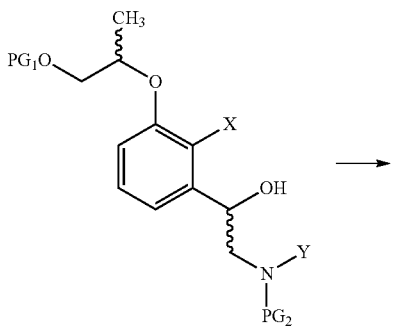

[Chemical Formula 14]

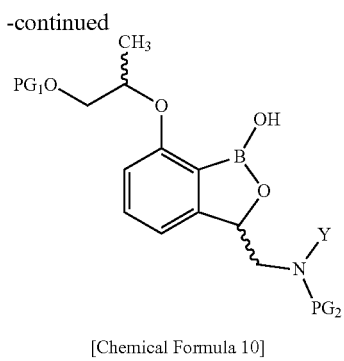

[Chemical Formula 10]

performing a intra-cyclization reaction of the compound of Chemical Formula 10 to remove the protecting group ($PG_1$) and then performing a cyclization reaction to prepare a tricyclic benzoxaborole compound of Chemical Formula 11; and

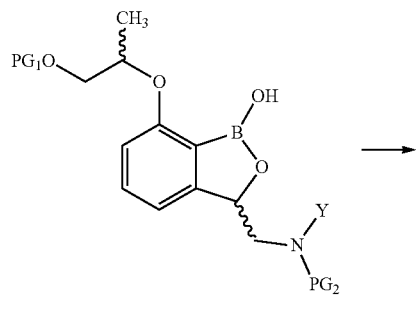

[Chemical Formula 10]

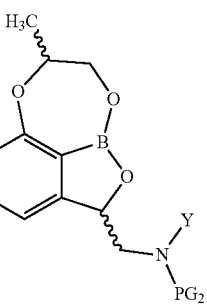

[Chemical Formula 11]

deprotecting the amino group of the compound of Chemical Formula 11 to prepare the compound of Chemical Formula 1.

In Chemical Formula 4 to 14, $PG_1$ and $PG_2$ are protecting groups for protecting active groups, and each independently, benzyl, t-butyl, Boc (tert-butyloxycarbonyl), pmb (4-methoxybenzyl), Fmoc (Fluorenylmethyloxycarbonyl), Ts (tosylate), MOM (methoxymethyl), THP (tetrahydropyranyl), TBDMS (tert-butyldimethylsilyl), or TBDPS (tert-butyldimethylsilyl), LG is a leaving group that leaves during the condensation reaction, and is halogen, para-toluenesulfonyl group or a methanesulfonyl group, X is hydrogen, halogen, or trifluoromethanesulfonyl, and Y is hydrogen or $PG_2$.

In a specific embodiment of the present invention, the borylation reaction may be performed using bis (pinacolato) diboron or 2-isopropoxy-4,4,5,5-tetramethyl-1,3,2-dioxaborolan, but is not limited thereto.

In another embodiment of the present invention, a pharmaceutical composition, in particular, a pharmaceutical composition of antibacterial agent against Gram-negative bacteria, including one or more selected from the group consisting of the compound of Chemical Formula 1, the isomers thereof and the pharmaceutically acceptable salts thereof as an active ingredient, is provided.

One embodiment of the present invention provides a method for preventing or treating Gram-negative bacterial infections, including the step of administering a therapeutically effective amount of the tricyclic benzoxaborole compound according to the present invention to a subject in need of prevention and/or treatment of diseases associated with Gram-negative bacterial infection. Before the administration step, the method may further include the step of determining whether the patient is in need of prevention and/or treatment of diseases associated with Gram-negative bacterial infection.

In an additional embodiment, the present invention relates to use of the antibiotic against Gram-negative bacteria including one or more selected from the group consisting of the compound of Chemical Formula 1, the isomers thereof and the pharmaceutically acceptable salts thereof as an active ingredient, or use thereof for the prevention and/or treatment of Gram-negative bacterial infections.

The compound of Chemical Formula 1, the isomers thereof and the pharmaceutically acceptable salts thereof used in the pharmaceutical composition, therapeutic method and use according to the present invention are the same as described above.

The novel tricyclic benzoxaborole compound according to the present invention is a broad-spectrum antibiotic against Gram-negative bacteria, in particular, multi-drug resistant Gram-negative bacteria, and for example, it exhibits excellent antibacterial activity against *Acinetobacter baumannii*, thereby being effectively used as a novel antibiotic substance. The Gram-negative bacteria are preferably, more preferably, carbapenem-resistant Gram-negative bacteria. Specific examples of the Gram-negative bacteria may include *A. baumannii, C. freundii, E. coli, E. cloacae, E. aerogenes, K. pneumoniae, K. oxytoca, M. morganii, P. aeruginosa P. vulgaris, P. mirabilis N. gonorrhoeae* or *S. marcescens*. Most preferably, the present invention relates to an antibiotic pharmaceutical composition against carbapenem-resistant *Acinetobacter baumannii* (*A. baumannii*).

The pharmaceutical composition including the compound of Chemical Formula 1, the isomer thereof or the pharmaceutically acceptable salt thereof as an active ingredient may be prepared in the form of a typical drug formulation. For example, the drug formulation may be prepared in a variety of formulations for oral or parenteral administration, and the type of the formulation may differ, depending on the use, administration method, administration purpose, etc.

When prepared in a variety of formulations for oral or parenteral administration, it may be formulated using one or more selected from the group consisting of diluents, excipients, etc., such as a typical filler, a bulking agent, a binder, a wetting agent, a disintegrating agent, or a surfactant.

A solid formulation for oral administration may include a tablet, a pill, powder, a granule, and a capsule, and these solid formulations are prepared by mixing the active ingredient with at least one excipient, for example, selected from the group consisting of starch, calcium carbonate, sucrose, lactose, gelatin, etc. In addition to the simple excipient, a lubricant, such as magnesium stearate, talc, etc. may be used. As a liquid formulation for oral administration, a suspension, a liquid for internal use, an emulsion, a syrup or the like may be used. When prepared to the liquid formulation, commonly used simple diluents such as water and/or liquid paraffin may be used. Arbitrarily, one or more selected from the group consisting of various other excipients, for example, a wetting agent, a sweetener, a flavoring agent, a preserving agent, etc. may be further included.

The parenteral administration may be performed via a route such as intravenous, intramuscular, subcutaneous, intraperitoneal, intranasal, or percutaneous administration. A formulation for the parenteral administration includes sterile aqueous or non-aqueous solutions, suspensions, emulsions, lyophilized formulations, suppositories, etc. As the non-aqueous solvent for the preparation of non-aqueous solutions or as the suspending solvent for the preparation of suspensions, propylene glycol, polyethylene glycol, a plant oil such as olive oil, an injectable ester such as ethylolate, etc. may be used. As a base for suppositories, witepsol, macrogol, tween 61, cacao butter, laurin butter, glycerogelatin, etc. may be used.

The content of one or more active ingredients selected from the group consisting of the compound of Chemical Formula 1, the isomers thereof and the pharmaceutically acceptable salts thereof in the pharmaceutical composition may be, for example, 0.001 to 99.9% by weight, 0.01 to 90% by weight, or 0.1 to 50% by weight, but is not limited thereto. It can be properly controlled, depending on the type of the formulation, administration method, administration purpose, etc.

Furthermore, the pharmaceutically effective amount of the pharmaceutical composition of the present invention which includes the compound of Chemical Formula 1, the isomer thereof and/or the pharmaceutically acceptable salt thereof as an active ingredient may be in the range of approximately 0.1 to approximately 1,000 mg/day. The pharmaceutically effective amount may be injected or administered once or several times per day, considering a patient's weight, age, sex, health conditions, and diet, administration time, administration method, excretion rate, severity of the disease, etc., but is not limited thereto. It is possible to administer the composition with various doses and methods of administration.

Further, if the tricyclic benzoxaborole derivative of the present invention is for oral administration, the compound of Chemical Formula 1 or the pharmaceutically acceptable salt thereof may be included in an amount of 1 to 95% by weight, and preferably, 1 to 70% by weight in the formulation.

The patient may be mammals, for example, primates including humans, rodents including mice, rats, etc., and specifically humans. For example, the patient may be a mammal, for example, humans whose symptoms or diseases can be prevented, improved, and/or treated by administration of the compound according to the present invention.

Technical Field

The tricyclic benzoxaborole compound according to the present invention has a broad antibacterial spectrum against resistant bacteria, low toxicity, and excellent antibacterial activity against Gram-negative bacteria, in particular, antibiotic-resistant Gram-negative bacteria, for example, *Acinetobacter baumannii*, and thus exhibits potent antibacterial effects on a variety of pathogenic bacteria in humans and animals. Therefore, it can be effectively used as an antibiotic against Gram-negative bacteria or in the prevention, improvement, and/or treatment of diseases associated with Gram-negative bacterial infection.

EXAMPLE

Hereinafter, the preferred Examples and Experimental Examples are provided for better understanding. However, these Examples and Experimental Examples are for illustrative purposes only, and the invention is not intended to be limited by these Examples.

Unless otherwise specified, all the reagents used below were purchased from Aldrich Korea, Acros, Lancaster, TCI, Alfa aesar, etc., and 1H NMR was performed on Varian 400 MHz, 600 MHz.

Example 1

Preparation of (7-methyl-7,8-dihydro-2H-1,6,9-trioxa-9a-borabenzo[cd]azulen-2-yl)methanamine hydrochloride

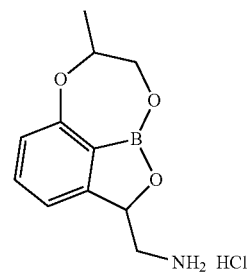 [SMILES: CC1COB2OC(CN)c3cccc(c32)O1 ; Cl]

[Step ]1 Preparation of 1-(benzyloxy)propan-2-ol

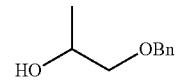

1,2-propanediol (5 g, 65.7 mmol) and NaH (3.29 g, 82.0 mmol) were dissolved in N,N-dimethylformamide (70 mL). benzyl bromide (7.82 mL, 65.7 mmol) was added at 0° C., followed by stirring for 2 hr. After reaction was finished, extraction was performed with water and ethyl acetate. The organic layer was dried over anhydrous sodium sulfate, filtered, and concentrated. The residue was purified by a column chromatography. The title compound (4.45 g, 41%) was produced.

$^1$H-NMR (CDCl$_3$, Varian 400 MHz): δ 1.15 (3H, d, J=6.4 Hz), 2.37 (1H, brs), 3.28 (1H, dd, J=9.4, 8.2 Hz), 3.47 (1H, dd, J=9.4, 3.0 Hz), 3.98-4.02 (1H, m), 4.56 (2H, s), 7.25-7.38 (5H, m).

[Step 2]Preparation of 1-(benzyloxy)propan-2-yl methanesulfonate

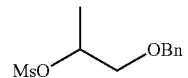

1-(benzyloxy)propan-2-ol (4.5 g, 27.1 mmol) prepared by Step 1 was dissolved in pyridine (50 mL). Methane sulfonyl chloride (2.32 ml, 29.8 mmol) was added at 0° C., followed by stirring at room temperature for 3 hr. After reaction was finished, extraction was performed with water and ethyl acetate. The organic layer was dried over anhydrous sodium sulfate, filtered, and concentrated. The residue was purified by a column chromatography. The title compound (6.00 g, 91%) was produced.

$^1$H-NMR (CDCl$_3$, Varian 400 MHz): δ 1.25 (3H, d, J=6.4 Hz), 3.01 (3H, s), 3.51-3.61 (2H, m), 4.56 (2H, d, J=2.0 Hz), 4.89-4.94 (1H, m), 7.26-7.37 (5H, m).

[Step 3]Preparation of 3-((1-(benzyloxy)propan-2-yl)oxy)-2-bromobenzaldehyde

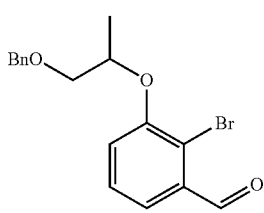 [SMILES: CC(COCc1ccccc1)Oc1cccc(C=O)c1Br]

1-(benzyloxy)propan-2-yl methanesulfonate (3.65 g, 14.9 mmol) prepared by Step 2 and 2-bromo-3-hydroxybenzaldehyde (3.00 g, 14.9 mmol) were dissolved in N,N-dimethylformamide (50 mL). K$_2$CO$_3$ (4.13 g, 29.8 mmol) was added, followed by stirring with reflux at 100° C. for 16 hr. After reducing the temperature of the reactant to room temperature, extraction was performed with water and ethyl acetate. The organic layer was dried over anhydrous sodium sulfate, filtered, and concentrated. The residue was purified by a column chromatography. The title compound (4.06 g, 78%) was produced.

$^1$H-NMR (CDCl$_3$, Varian 400 MHz): δ 1.40 (3H, d, J=6.4 Hz), 3.65 (1H, dd, J=10.0, 4.0 Hz), 3.75 (1H, dd, J=10.4, 6.4 Hz), 4.61-4.65 (3H, m), 7.23 (1H, dd, J=8.2, 1.4 Hz), 7.28-7.35 (6H, m), 7.52 (1H, dd, J=8.2, 1.0 Hz), 10.43 (1H, d, J=0.4 Hz).

[Step 4]Preparation of 3-((1-(benzyloxy)propan-2-yl)oxy)-2-(4,4,5,5-tetramethyl-1,3,2-dioxaborolan-2-yl)benzaldehyde

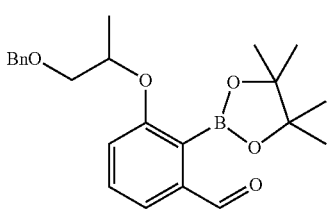 [SMILES: CC(COCc1ccccc1)Oc1cccc(C=O)c1B1OC(C)(C)C(C)(C)O1]

3-((1-(benzyloxy)propan-2-yl)oxy)-2-bromobenzaldehyde (3.00 g, 8.59 mmol) prepared by Step 3 was dissolved in dioxane (60 mL). 1,1'-bis (diphenylphosphino)ferrocene dichloropalladium (314 mg, 0.43 mmol), potassium acetate (1.68 g, 17.2 mmol), and bis (pinacolato)diboron (4.36 g, 17.2 mmol) were added, followed by stirring with reflux at 100° C. for 1 hr. After reducing the temperature of the reactant to room temperature, extraction was performed with water and ethyl acetate. The organic layer was dried over anhydrous sodium sulfate, filtered, and concentrated. The residue was purified by a column chromatography. The title compound (700 mg, 20%) was produced.

$^1$H-NMR (CDCl$_3$, Varian 400 MHz): δ 1.35 (3H, d, J=6.0 Hz), 1.43 (12H, s), 3.64 (1H, dd, J=10.0, 5.2 Hz), 3.69 (1H, dd, J=10.0, 5.6 Hz), 4.55 (2H, d, J=3.2 Hz), 4.60 (1H, dd, J=12.0, 5.6 Hz), 7.18 (1H, d, J=8.0 Hz), 7.27-7.34 (5H, m), 7.38 (1H, d, J=6.4 Hz), 7.43 (1H, t, J=7.8 Hz), 9.92 (1H, s).

[Step 5]Preparation of 7-((1-(benzyloxy)propan-2-yl)oxy)-1-hydroxy-1,3-dihydrobenzo[c][1,2]oxaborole-3-carbonitrile

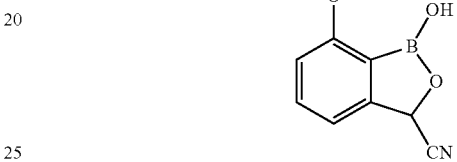

3-((1-(benzyloxy)propan-2-yl)oxy)-2-(4,4,5,5-tetramethyl-1,3,2-dioxaborolan-2-yl)benzaldehyde (700 mg, 1.76 mmol) prepared by Step 4 was dissolved in water (1 ml) and tetrahydrofuran (1 ml). Sodium cyanide (87 mg, 1.78 mmol) was added at room temperature. After stirring 1 hr, the reactant was added by 2N hydrochloric acid to pH 1. After reaction was finished, extraction was performed with ethyl acetate. The organic layer was dried over anhydrous sodium sulfate, filtered, and concentrated. The residue was purified by a column chromatography. The title compound (500 mg, 88%) was produced.

$^1$H-NMR (CDCl$_3$, Varian 400 MHz): δ 1.21-1.24 (3H, m), 3.59-3.70 (2H, m), 4.30-4.42 (1H, m), 4.43-4.52 (1H, m), 4.66-4.77 (2H, m), 5.79 (1H, s), 5.82 (1H, s), 7.01 (1H, d, J=8.0 Hz), 7.25-7.39 (5H, m), 7.53 (1H, td, J=7.7, 1.9 Hz), 8.13 (1H, s), 8.26 (1H, s).

[Step 6]Preparation of t-butyl ((7-((1-(benzyloxy)propan-2-yl)oxy)-1-hydroxy-1,3-dihydrobenzo[c][1,2]oxaborole-3-yl)methyl)carbamate

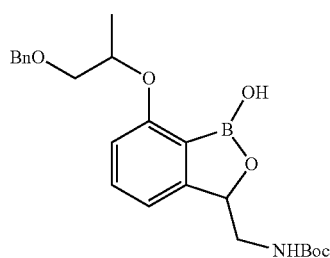 [SMILES: CC(COCc1ccccc1)Oc1cccc2c1B(O)OC2CNC(=O)OC(C)(C)C]

7-((1-(benzyloxy)propan-2-yl)oxy)-1-hydroxy-1,3-dihydrobenzo[c][1,2]oxaborole-3-carbonitrile (500 mg, 1.55 mmol) prepared by Step 5 was dissolved in anhydrous tetrahydrofuran (10 ml). 1M borane tetrahydrofuran complex (3.1 ml) reagent was added slowly at room temperature. Afterward, the reactant was stirred with reflux for 3 hr, and then the temperature of the reactant was reduced by cooling slowly to room temperature. After the reactant was added by methanol slowly, azeotropic distillation was performed with concentration under reduced pressure. After repeating the above process three times using methanol (10 ml) three times, the concentrated reactant was dissolved in tetrahydrofuran (10 ml). The reactant was added by triethylamine (0.42 ml) and di-t-butyl dicarbonate (0.35 ml) in orderm, and then stirred at room temperature for 4 hr. After the reactant was added by 2N hydrochloric acid to acidic, extraction was performed with ethyl acetate twice. The organic layer was dried over anhydrous sodium sulfate, filtered, and concentrated. The residue was purified by a column chromatography. The title compound (340 mg, 51%) was produced.

$^1$H-NMR (CDCl$_3$, Varian 400 MHz): δ 1.22 (3H, d, J=6.4 Hz), 1.42 (9H, s), 2.98-3.08 (1H, m), 3.58-3.69 (2H, m), 3.82-3.95 (1H, m), 4.36-4.43 (1H, m), 4.64-4.76 (1H, m), 4.96-5.08 (1H, m), 5.19-5.24 (1H, m), 6.89 (1H, d, J=7.6 Hz), 7.09 (1H, d, J=7.6 Hz), 7.31-7.46 (6H, m), 7.53 (1H, s), 7.60 (1H, s).

[Step 7] Preparation of t-butyl ((7-methyl-7,8-dihydro-2H-1,6,9-trioxa-9a-borabenzo[cd]azulen-2-yl)methyl)carbamate

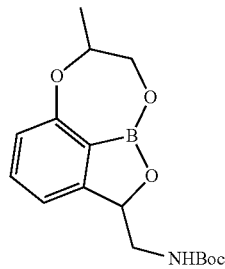 [SMILES: CC1COB2OC(CNC(=O)OC(C)(C)C)c3cccc(c32)O1]

t-butyl ((7-((1-(benzyloxy)propan-2-yl)oxy)-1-hydroxy-1,3-dihydrobenzo[c][1,2]oxaborole-3-yl)methyl)carbamate (200 mg, 0.439 mmol) prepared by Step 6 and palladium hydroxy(12.3 mg, 0.088 mmol) were dissolved in methanol (5 ml), followed by stirring with hydrogen reaction for 1 hr. After the reaction solution was filtered by Celite using ethyl acetate, the residue solution was filtered under reduced pressure. The title compound (140 mg, 89%) was produced.

$^1$H-NMR (CDCl$_3$, Varian 400 MHz): δ 1.42 (9H, s), 1.47 (3H, d, J=6.8 Hz), 2.98-3.08 (1H, m), 3.80-3.93 (1H, m), 4.22 (2H, s), 4.18-4.42 (1H, m), 4.90-5.18 (1H, m), 5.30-5.37 (1H, m), 6.85 (1H, d, J=8.0 Hz), 6.98 (1H, d, J=7.2 Hz), 7.42 (1H, t, J=7.8 Hz).

[Step 8] Preparation of (7-methyl-7,8-dihydro-2H-1,6,9-trioxa-9a-borabenzo[cd]azulen-2-yl) methanamine hydrochloride

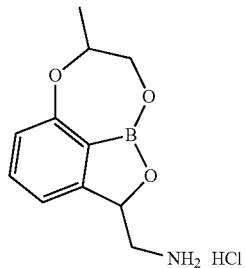 [SMILES: CC1COB2OC(CN)c3cccc(c32)O1 ; Cl]

t-butyl((7-methyl-7,8-dihydro-2H-1,6,9-trioxa-9a-borabenzo[cd]azulen-2-yl)methyl)carbamate (140 mg, 0.439 mmol) prepared by Step 7 was dissolved in dioxane (5 ml). Hydrochloric acid solution (4N dioxane solution, 3.29 ml, 13.1 mmol) was added at 0° C. The reaction solution was stirred at room temperature for 16 hr, concentrated under reduced pressure to removing solvent, and dissolved in ethyl ether. The obtained solid was filtered. The title compound (92.0 mg, 96%) was produced.

$^1$H-NMR (CD$_3$OD, Varian 400 MHz): δ 1.43 (3H, s), 2.91-2.99 (1H, m), 3.58 (1H, td, J=13.0, 2.7 Hz), 4.15-4.42 (3H, m), 5.46 (1H, t, J=10.4 Hz), 6.88 (1H, d, J=8.0 Hz), 7.03 (1H, d, J=7.2 Hz), 7.47 (1H, t, J=7.8 Hz).

Example 2

Preparation of ((2S)-7-methyl-7,8-dihydro-2H-1,6,9-trioxa-9a-borabenzo[cd]azulen-2-yl)methanamine hydrochloride

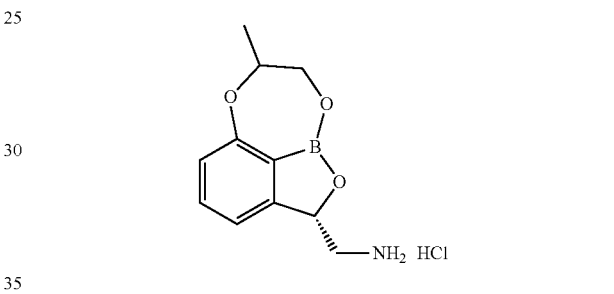

[Step 1] Preparation of 1-(benzyloxy)propan-2-yl methanesulfonate

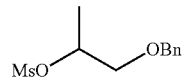

Starting compound 1-(benzyloxy)propan-2-ol (36 g, 217 mmol) and diisopropylethylamine (39.2 g, 303 mmol) were dissolved in toluene (540 mL). methane sulfonyl chloride (2.32 ml, 29.8 mmol) was added at 0° C., followed by stirring for 2 hr and stirring more at room temperature for 1 hr. After reaction was finished, extraction was performed with water (500 ml) and toluene (200 ml, twice). The organic layer was extracted by saturated ammonium chloride aqueous solution (200 ml) and saturated sodium chloride aqueous solution (200 ml), and washed. The organic layer was dried over anhydrous sodium sulfate, filtered, and concentrated. The residue was dried. The title compound (53 g) was produced.

$^1$H-NMR (CDCl$_3$, Varian 400 MHz): δ 1.40 (3H, d, J=6.4 Hz), 3.01 (3H, s), 3.52-3.61 (2H, m), 4.55 & 4.57 (2H, ABq, J$_{AB}$=11.8 Hz), 4.88-4.96 (1H, m), 7.26-7.38 (5H, m).

[Step 2]Preparation of
3-((1-(benzyloxy)propan-2-yl)oxy) benzaldehyde

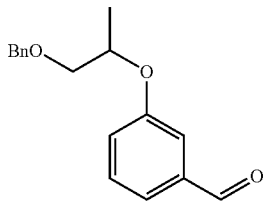 [SMILES: CC(COCc1ccccc1)Oc1cccc(C=O)c1]

Starting compound 3-hydroxy benzaldehyde (26.5 g, 217 mmol) and potassium carbonate (36.0 g, 261 mmol) were dissolved in dimethylformamide (540 mL), followed by stirring at 0° C. for 30 minutes. 1-(benzyloxy)propan-2-yl methanesulfonate (53 g, 217 mmol) prepared by Step 1 of EXAMPLE 1 was added slowly, followed by stirring at 100° C. for 10 hr. The reactant was cooled to room temperature. The reactant was extracted with ice water (1 L) and heptane (500 ml, twice). The organic layer was extracted with 0.02N sodium hydroxide aqueous solution (200 ml, twice), 0.01N hydrochloric acid aqueous solution (200 ml) and saturated sodium chloride aqueous solution (200 ml), and washed. The organic layer was dried over anhydrous sodium sulfate, filtered, and concentrated. The residue was dried. The title compound (46 g, 78%) was produced.

$^1$H-NMR (CDCl$_3$, Varian 400 MHz): δ 1.35 (3H, d, J=6.0 Hz), 3.68 (1H, dd, J=10.4, 6.0 Hz), 3.59 (1H, dd, J=10.0, 4.4 Hz), 4.59 (2H, s), 4.63-4.71 (1H, m), 7.18-7.21 (1H, m), 7.28-7.36 (5H, m), 7.40-7.46 (3H, m), 9.95 (1H, s).

[Step 3]Preparation of (1S)-1-(3-((1-(benzyloxy)propan-2-yl)oxy)phenyl)-2-nitroethan-1-ol

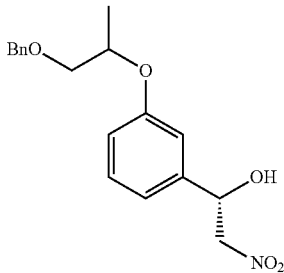

Copper acetate monohydrate (0.739 g, 3.70 mmol) and (1R)-1,7,7-trimethyl-N-(pyridine-2-ylmethyl)bicyclo[2.2.1]heptane-2-amine (0.994 g, 4.07 mmol) were dissolved in ethanol (110 mL), followed by stirring at room temperature for 1 hr. After adding nitromethane (22.6 g, 370 mmol) to reactant slowly, the reactant was stirred at −30° C. for 30 minutes. 3-((1-(benzyloxy)propan-2-yl)oxy) benzaldehyde (20 g, 74 mmol) prepared by Step 1 was diluted in ethanol (40 ml), and added to the reactant maintaining −30° C. slowly for about more than 1 hr. The −30° C. reactant being stirred was added by diisopropylethylamine (1.29 ml, 7.40 mmol), stirred at same temperature for more than 24 hr, and heated slowly to room temperature. The reactant was extracted with 1N hydrochloric acid aqueous solution (300 ml) and dichloromethane (300 ml), and the aqueous layer was more extracted with dichloromethane (80 ml, twice). The organic layer was extracted by saturated sodium chloride aqueous solution (100 ml), and washed. The organic layer was dried over anhydrous sodium sulfate, filtered, and concentrated. The residue was dried. The title compound (25.3 g) was produced.

$^1$H-NMR (CDCl$_3$, Varian 400 MHz): δ 1.33 (3H, m), 2.90 (1H, brs), 3.54-3.59 (1H, m), 3.61-3.69 (1H, m), 4.45 (1H, m), 4.50-4.62 (4H, m), 5.38 (1H, m), 6.86-6.99 (3H, m), 7.24-7.38 (6H, m).

[Step 4]Preparation of (1S)-2-amino-1-(3-((1-(benzyloxy)propan-2-yl)oxy)phenyl)ethan-1-ol

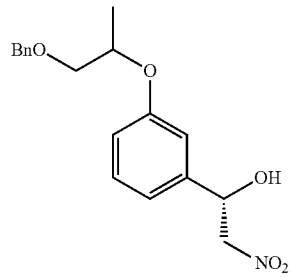

(1S)-1-(3-((1-(benzyloxy)propan-yl)oxy)phenyl)-2-nitroethan-1-ol (25.3 g, 76.0 mmol) prepared by Step 3 was dissolved in ethanol (381 mL). 5% palladium/active carbon (4.06 g, 1.91 mmol) and 5% platinum/active carbon (1.01 g, 0.259 mmol) was added as catalyst. After performing hydrogen reaction at room temperature (about 25° C.) under 50~60 psi pressure for more than 9 hr, filtration was performed using celite to removing palladium and platinum. The filtrate was dried over anhydrous sodium sulfate, filtered, and concentrated. The residue was dried. The title compound (22.2 g, 97%) was produced.

[Step 5]Preparation of (1S)-1-(3-((1-(benzyloxy)propan-2-yl)oxy)phenyl)-2-(dibenzylamino)ethan-1-ol hydrochloride

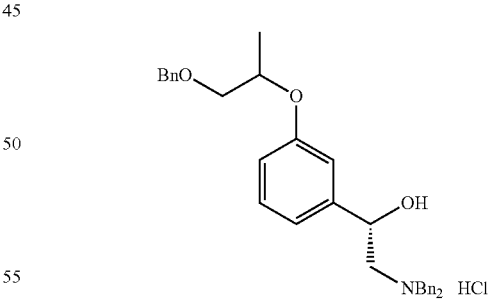

(1S)-2-amino-1-(3-((1-(benzyloxy)propan-2-yl)oxy)phenyl)ethan-1-ol (22.2 g, 73.6 mmol) prepared by Step 4 was dissolved in ethanol (245 ml). potassium carbonate (22.4 g, 162 mmol) was added, followed by stirring at room temperature for about 15 hr. The reactant was added by methyl tertiary-butyl ether (100 ml), cooled to 0° C., and stirred for 30 minutes. After the obtained solid precipitate was filtered using celite, the filtrate was added by saturated hydrochloric acid solution (12.3 ml, 147 mmol), and stirred for 30 minutes. After removing methyl tertiary-butyl ether and excess hydrochloric acid by concentration, azeotropic distillation was performed using isopropanol (100 ml) to remove remaining water. After removing water by repeating azeotropic distillation two or three time, the remaining solid was added by isopropanol (45 ml), and stirred at 60° C. for 2 hr to dissolve the solid. After cooling to room temperature slowly again, stir was performed for 2 hr. Methyl tertiary-butyl ether was added slowly at room temperature for 1 hr when starting to produce a solid, followed by stirring for 2 hr additionally. After the obtained white solid was filtered, the filtered solid washed with methyl tertiary-butyl ether (50 ml). The solid was dried under reduced pressure. The title compound (20.4 g, 54%) was produced in whige solid phase.

$^1$H-NMR (CDCl$_3$, Varian 400 MHz): δ 1.28 (3H, d, J=6.0 Hz), 2.98-3.03 (1H, m), 3.13-3.22 (1H, m), 3.53 (1H, dd, J=10.2, 4.6 Hz), 3.59-3.64 (1H, m), 4.15-4.18 (1H, m), 4.34 (1H, dd, J=13.2, 5.2 Hz), 4.46-4.55 (3H, m), 4.57 (2H, s), 5.07 (1H, d, J=9.6 Hz), 5.42 (1H, s), 6.62 (1H, d, J=6.6 Hz), 6.75 (1H, brs), 6.80 (1H, dd, J=8.0, 2.4 Hz), 7.15 (1H, t, J=7.8 Hz), 7.26-7.35 (5H, m), 7.44-7.51 (6H, m), 7.61-7.63 (2H, m), 7.67-7.72 (2H, m), 12.06 (1H, brs).

[Step 6]Preparation of (3S)-7-((1-(benzyloxy)propan-2-yl)oxy)-3-((dibenzylamino)methyl)benzo[c][1,2]oxaborole-1 (3H)-ol

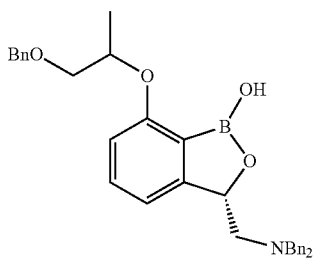

(1S)-1-(3-((1-(benzyloxy)propan-2-yl)oxy)phenyl)-2-(dibenzylamino)ethan-1-ol hydrochloride (10 g, 19.3 mmol) prepared by Step 4 was dissolved in anhydrous toluene (77 ml) in flask (A) filled with nitrogen. After the reactant which was not totally dissolved was heated to 40-45° C. maintaining the state of nitrogen filled, normal butyllithium (2.5M hexane solution, 8.49 ml, 21.2 mmol) was added slowly for about 1 hr. After stirring 1 hr, the reactant was cooled to −30° C., stirred, and added by normal butyllithium (2.5M hexane solution, 37.82 ml, 94.3 mmol) slowly for about 1 hr maintaining the state of nitrogen filled. The temperature of the reactant was not to exceed −20° C. 2-isopropoxy-4,4,5,5-tetramethyl-1,3,2-dioxaborolane (31.2 ml, 154 mmol) was dissolved using tetrahydrofuran (9 ml) and anhydrous toluene (77 ml) in another flask (B), followed by stirring at −40° C. The reactant of (B) flask was added by the reactant of (A) flask slowly in drop-wise manner for about 2 hr. After stirring at same temperature for another 1 hr, the reactant was heated to 10° C. slowly for 1 hr. The stirring reactant was added by 5% sodium bicarbonate aqueous solution (150 ml) in drop-wise manner. The reactant of suspension was filtered, and the filtrate was washed by ethyl acetate (50 ml). After the aqueous layer of the filtrate was extracted with ethyl acetate (100 ml) twice, the all organic layer was washed with saturated sodium chloride aqueous solution (100 ml), dried over anhydrous sodium sulfate, filtered, and concentrated. The residue was purified by a column chromatography. The title compound (6.03 g, 62%) was produced.

$^1$H-NMR (CDCl$_3$, Varian 400 MHz): δ 1.21 (3H, d, J=6.4 Hz), 2.67 (1H, dd, J=14.0, 7.6 Hz), 2.99 (1H, dd, J=14.4, 3.6 Hz), 3.56 (1H, dd, J=10.0, 2.8 Hz), 3.63 (1H, dd, J=10.0, 8.0 Hz), 3.74 (2H, d, J=13.6 Hz) 3.90 (2H, d, J=13.6 Hz), 4.36-4.42 (1H, m), 4.65 & 4.72 (2H, ABq, J$_{AB}$=12.4 Hz), 5.35-5.38 (1H, m), 6.76-6.83 (2H, m), 7.19-7.38 (16H, m).

[Step 7]Preparation of ((2S)-7-methyl-7,8-dihydro-2H-1,6,9-trioxa-9a-borabenzo[cd]azulen-2-yl)methanamine hydrochloride

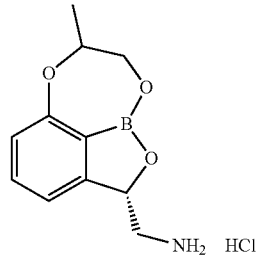

(3S)-7-((1-(benzyloxy)propan-2-yl)oxy)-3-((dibenzylamino)methyl)benzo[c][1,2]oxaborole-1 (3H)-ol (5.56 g, 11.0 mmol) of Step 6 was dissolved using the mixed solution of 1N hydrochloric acid aqueous solution (13.2 ml, 13.2 mmol) and methanol (110 ml) at room temperature. 5% palladium/active carbon catalyst was added to reactant. The reactant was heated to 50° C., and filled with hydrogen gas under 50~60 psi pressure while being stirred. After performing reaction maintaining the above state for more than 10 hr, the reactant was filtered using celite to removing palladium. The filtered celite layer was washed with methanol (10 ml), and then the filtrate was concentrated. The filtrate was added by isopropanol (50 ml), azeotropic distillation was performed to remove water. After removing water by performing azeotropic distillation two or three times, the obtained solid was added by isopropanol (7 ml), stirred for more than 5 hr, and the suspension was filtered. The obtained solid was washed with isopropanol (3 ml). The filtered solid, which was gathered, was dried under reduced pressure. The title compound (2.4 g, 86%) was produced.

$^1$H-NMR (DMSO-d6, Varian 400 MHz): δ 1.40 (3H, s), 2.82-2.93 (1H, m), 3.45-3.57 (1H, m), 4.14-4.30 (3H, m), 5.50-5.60 (1H, m), 6.79-6.83 (1H, m), 7.10-7.15 (1H, m), 7.48 (1H, t, J=7.8 Hz), 8.40 (3H, brs).

Example 3

Preparation of ((2S,7R)-7-methyl-7,8-dihydro-2H-1,6,9-trioxa-9a-borabenzo[cd]azulen-2-yl)methanamine hydrochloride

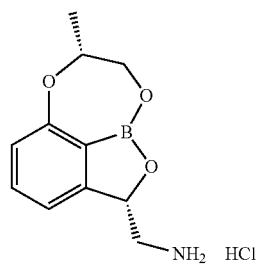 [SMILES: C[C@@H]1COB2O[C@H](CN)c3cccc(c32)O1 ; Cl]

[Step 1] Preparation of (S)-1-(benzyloxy)propan-2-yl methanesulfonate

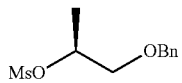

Starting compound (S)-1-(benzyloxy)propan-2-ol (36 g, 217 mmol) and diisopropylethylamine (39.2 g, 303 mmol) were dissolved in toluene (540 mL). methane sulfonyl chloride (2.32 ml, 29.8 mmol) was added at 0° C., followed by stirring for 2 hr and stirring more at room temperature for 1 hr. After reaction was finished, extraction was performed with water (500 ml) and toluene (200 ml, twice). The organic layer was extracted by saturated ammonium chloride aqueous solution (200 ml) and saturated sodium chloride aqueous solution (200 ml), and washed. The organic layer was dried over anhydrous sodium sulfate, filtered, and concentrated. The residue was dried. The title compound (53 g) was produced.

$^1$H-NMR (CDCl$_3$, Varian 400 MHz): δ 1.40 (3H, d, J=6.4 Hz), 3.01 (3H, s), 3.52-3.61 (2H, m), 4.55 & 4.57 (2H, ABq, J$_{AB}$=11.8 Hz), 4.88-4.96 (1H, m), 7.26-7.38 (5H, m).

[Step 2] Preparation of (R)-3-((1-(benzyloxy)propan-2-yl)oxy) benzaldehyde

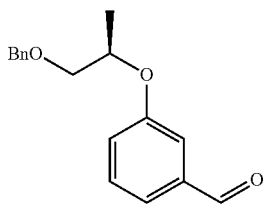 [SMILES: C[C@H](COCc1ccccc1)Oc1cccc(C=O)c1]

Starting compound 3-hydroxy benzaldehyde (26.5 g, 217 mmol) and potassium carbonate (36.0 g, 261 mmol) were dissolved in dimethylformamide (540 mL), followed by stirring at 0° C. for 30 minutes. (S)-1-(benzyloxy)propan-2-yl methanesulfonate (53 g, 217 mmol) prepared by Step 1 was added slowly, followed by stirring at 100° C. for 10 hr. The reactant was cooled to room temperature. The reactant was extracted with ice water (1 L) and heptane (500 ml, twice). The organic layer was extracted with 0.02N sodium hydroxide aqueous solution (200 ml, twice), 0.01N hydrochloric acid aqueous solution (200 ml) and saturated sodium chloride aqueous solution (200 ml), and washed. The organic layer was dried over anhydrous sodium sulfate, filtered, and concentrated. The residue was dried. The title compound (46 g, 78%) was produced.

$^1$H-NMR (CDCl$_3$, Varian 400 MHz): δ 1.35 (3H, d, J=6.0 Hz), 3.68 (1H, dd, J=10.4, 6.0 Hz), 3.59 (1H, dd, J=10.0, 4.4 Hz), 4.59 (2H, s), 4.63-4.71 (1H, m), 7.18-7.21 (1H, m), 7.28-7.36 (5H, m), 7.40-7.46 (3H, m), 9.95 (1H, s).

[Step 3] Preparation of (S)-1-(3-(((R)-1-(benzyloxy)propan-2-yl)oxy)phenyl)-2-nitroethan-1-ol

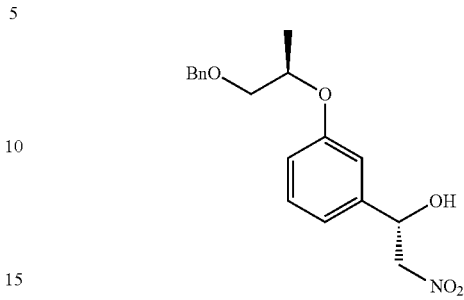

Copper acetate monohydrate (0.739 g, 3.70 mmol) and (1R)-1,7,7-trimethyl-N-(pyridine-2-ylmethyl)bicyclo[2.2.1]heptane-2-amine (0.994 g, 4.07 mmol) were dissolved in ethanol (110 mL), followed by stirring at room temperature for 1 hr. After adding nitromethane (22.6 g, 370 mmol) to reactant slowly, the reactant was stirred at −30° C. for 30 minutes. (R)-3-((1-(benzyloxy)propan-2-yl)oxy) benzaldehyde (20 g, 74 mmol) prepared by Step 2 was diluted in ethanol (40 ml), and added to the reactant maintaining −30° C. slowly for about more than 1 hr. The −30° C. reactant being stirred was added by diisopropylethylamine (1.29 ml, 7.40 mmol), stirred at same temperature for more than 24 hr, and heated slowly to room temperature. After the reactant was extracted with 1N hydrochloric acid aqueous solution (300 ml) and dichloromethane (300 ml), the aqueous layer was more extracted with dichloromethane (80 ml, twice). The organic layer was extracted by saturated sodium chloride aqueous solution (100 ml), and washed. The organic layer was dried over anhydrous sodium sulfate, filtered, and concentrated. The residue was dried. The title compound (25.3 g) was produced.

$^1$H-NMR (CDCl$_3$, Varian 400 MHz): δ 1.33 (3H, d, J=6.4 Hz), 2.82 (1H, brs), 3.56 (1H, dd, J=10.4, 4.4 Hz), 3.66 (1H, dd, J=10.2, 6.2 Hz), 4.45 (1H, dd, J=13.4, 3.0 Hz), 4.51-4.60 (2H, m), 4.58 (2H, s), 5.39 (1H, dd, J=9.6, 2.8 Hz), 6.89-6.99 (3H, m), 7.26-7.37 (6H, m).

[Step 4] Preparation of (S)-2-amino-1-(3-(((R)-1-(benzyloxy)propan-2-yl)oxy)phenyl)ethan-1-ol

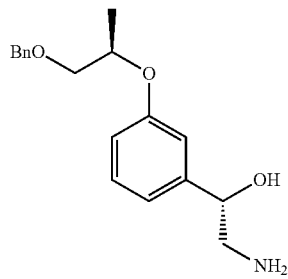 [SMILES: C[C@H](COCc1ccccc1)Oc1cccc([C@H](O)CN)c1]

(S)-1-(3-(((R)-1-(benzyloxy)propan-2-yl)oxy)phenyl)-2-nitroethan-1-ol (25.3 g, 76.0 mmol) prepared by Step 3 was dissolved in ethanol (381 mL). 5% palladium/active carbon (4.06 g, 1.91 mmol) and 5% platinum/active carbon (1.01 g, 0.259 mmol) was added as catalyst. After performing hydrogen reaction at room temperature (about 25° C.) under 50~60 psi pressure for more than 9 hr, filtration was performed using celite to removing palladium and platinum. The filtrate was dried over anhydrous sodium sulfate, filtered, and concentrated. The residue was dried. The title compound (22.2 g, 97%) was produced.

$^1$H-NMR (CDCl$_3$, Varian 400 MHz): δ 1.32 (3H, d, J=6.0 Hz), 2.39 (3H, brs), 2.79 (1H, dd, J=12.6, 7.8 Hz), 2.97 (1H, dd, J=13.0, 3.8 Hz), 3.55 (1H, dd, J=8.2, 3.0 Hz), 3.66 (1H, dd, J=10.2, 5.8 Hz), 4.58 (2H, s), 4.56-4.63 (2H, m), 6.83 (1H, dd, J=8.2, 1.8 Hz), 6.90 (1H, d, J=7.6 Hz), 6.95-6.96 (1H, m), 7.23 (1H, t, J=7.8 Hz), 7.35-7.25 (5H, m).

[Step 5]Preparation of (S)-1-(3-(((R)-1-(benzyloxy)propan-2-yl)oxy)phenyl)-2-(dibenzylamino)ethan-1-ol hydrochloride

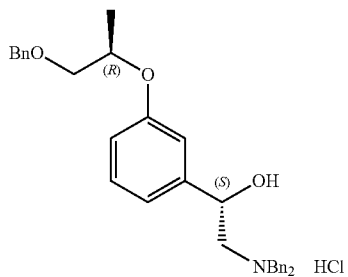

(S)-2-amino-1-(3-(((R)-1-(benzyloxy)propan-2-yl)oxy)phenyl)ethan-1-ol (22.2 g, 73.6 mmol) prepared by Step 4 was dissolved in ethanol (245 ml). potassium carbonate (22.4 g, 162 mmol) was added, followed by stirring at room temperature for about 15 hr. The reactant was added by methyl tertiary-butyl ether (100 ml), cooled to 0° C., and stirred for 30 minutes. After the obtained solid precipitate was filtered using celite, the filtrate was added by saturated hydrochloric acid solution (12.3 ml, 147 mmol), and stirred for 30 minutes. After removing methyl tertiary-butyl ether and excess hydrochloric acid by concentration, azeotropic distillation was performed using isopropanol (100 ml) to remove remaining water. After removing water by repeating azeotropic distillation two or three time, the remaining solid was added by isopropanol (45 ml), and stirred at 60° C. for 2 hr to dissolve the solid. After cooling to room temperature slowly again, stir was performed for 2 hr. Methyl tertiary-butyl ether was added slowly at room temperature for 1 hr when starting to produce a solid, followed by stirring for 2 hr additionally. After the obtained white solid was filtered, the filtered solid washed with methyl tertiary-butyl ether (50 ml). The solid was dried under reduced pressure. The title compound (20.4 g, 54%) was produced in whige solid phase.

$^1$H-NMR (CDCl$_3$, Varian 400 MHz): δ 1.28 (3H, d, J=6.0 Hz), 2.98-3.02 (1H, m), 3.15-3.21 (1H, m), 3.53 (1H, dd, J=10.2, 4.6 Hz), 3.62 (1H, dd, J=10.4, 6.0 Hz), 4.17 (1H, dd, J=13.4, 6.2 Hz), 4.33 (1H, dd, J=13.2, 5.2 Hz), 4.47-4.55 (3H, m), 4.57 (2H, s), 5.07 (1H, d, J=9.6 Hz), 5.42 (1H, s), 6.62 (1H, d, J=6.6 Hz), 6.75 (1H, brs), 6.80 (1H, dd, J=8.0, 2.4 Hz), 7.15 (1H, t, J=7.8 Hz), 7.26-7.35 (5H, m), 7.45-7.50 (6H, m), 7.62-7.64 (2H, m), 7.69-7.71 (2H, m), 12.06 (1H, brs).

[Step 6]Preparation of (S)-7-(((R)-1-(benzyloxy)propan-2-yl)oxy)-3-((dibenzylamino)methyl)benzo[c][1,2]oxaborole-1 (3H)-ol

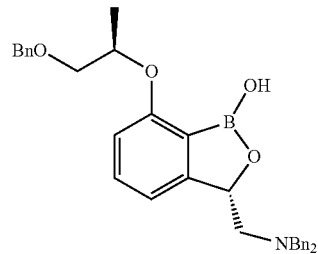

(S)-1-(3-(((R)-1-(benzyloxy)propan-2-yl)oxy)phenyl)-2-(dibenzylamino)ethan-1-ol hydrochloride (10 g, 19.3 mmol) prepared by Step 5 was dissolved in anhydrous toluene (77 ml) in flask (A) filled with nitrogen. After the reactant which was not totally dissolved was heated to 40-45° C. maintaining the state of nitrogen filled, normal butyllithium (2.5M hexane solution, 8.49 ml, 21.2 mmol) was added slowly for about 1 hr. After stirring 1 hr, the reactant was cooled to −30° C., stirred, and added by normal butyllithium (2.5M hexane solution, 37.82 ml, 94.3 mmol) slowly for about 1 hr maintaining the state of nitrogen filled. The temperature of the reactant was not to exceed −20° C. 2-isopropoxy-4,4,5,5-tetramethyl-1,3,2-dioxaborolane (31.2 ml, 154 mmol) was dissolved using tetrahydrofuran (9 ml) and anhydrous toluene (77 ml) in another flask (B), followed by stirring at −40° C. The reactant of (B) flask was added by the reactant of (A) flask slowly in drop-wise manner for about 2 hr. After stirring at same temperature for another 1 hr, the reactant was heated to 10° C. slowly for 1 hr. The stirring reactant was added by 5% sodium bicarbonate aqueous solution (150 ml) in drop-wise manner. The reactant of suspension was filtered, and the filtrate was washed by ethyl acetate (50 ml). After the aqueous layer of the filtrate was extracted with ethyl acetate (100 ml) twice, the all organic layer was washed with saturated sodium chloride aqueous solution (100 ml), dried over anhydrous sodium sulfate, filtered, and concentrated. The residue was purified by a column chromatography. The title compound (6.03 g, 62%) was produced.

$^1$H-NMR (CDCl$_3$, Varian 400 MHz): δ 1.21 (3H, d, J=6.4 Hz), 2.67 (1H, dd, J=14.0, 7.6 Hz), 2.99 (1H, dd, J=14.4, 3.6 Hz), 3.56 (1H, dd, J=10.0, 2.8 Hz), 3.63 (1H, dd, J=10.0, 8.0 Hz), 3.74 (2H, d, J=13.6 Hz) 3.89 (2H, d, J=13.6 Hz), 4.36-4.41 (1H, m), 4.65 & 4.72 (2H, ABq, J$_{AB}$=12.4 Hz), 5.35-5.38 (1H, m), 6.78-6.83 (2H, m), 7.20-7.39 (16H, m).

[Step 7]Preparation of ((2S, 7R)-7-methyl-7,8-dihydro-2H-1,6,9-trioxa-9a-borabenzo[cd]azulen-2-yl)methanamine hydrochloride

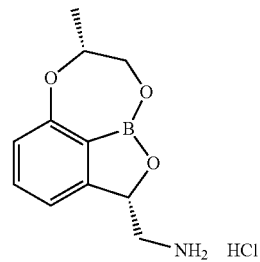 [SMILES: C[C@@H]1COB2O[C@H](CN)c3cccc(c32)O1 ; Cl]

(S)-7-(((R)-1-(benzyloxy)propan-2-yl)oxy)-3-((dibenzylamino)methyl)benzo[c][1,2]oxaborole-1 (3H)-ol (5.56 g, 11.0 mmol) of Step 6 was dissolved using the mixed solution of 1N hydrochloric acid aqueous solution (13.2 ml, 13.2 mmol) and methanol (110 ml) at room temperature. 5% palladium/active carbon catalyst was added to reactant. The reactant was heated to 50° C., and filled with hydrogen gas under 50~60 psi pressure while being stirred. After performing reaction maintaining the above state for more than 10 hr, the reactant was filtered using celite to removing palladium. The filtered celite layer was washed with methanol (10 ml), and then the filtrate was concentrated. The filtrate was added by isopropanol (50 ml), azeotropic distillation was performed to remove water. After removing water by performing azeotropic distillation two or three times, the obtained solid was added by isopropanol (7 ml), stirred for more than 5 hr, and the suspension was filtered. The obtained solid was washed with isopropanol (3 ml). The filtered solid, which was gathered, was dried under reduced pressure. The title compound (2.4 g, 86%) was produced.

$^1$H-NMR (DMSO-d6, Varian 400 MHz): δ 1.41 (3H, d, J=6.4 Hz), 2.87 (1H, dd, J=13.2, 9.2 Hz), 3.52 (1H, dd, J=13.2, 2.4 Hz), 4.15-4.26 (2H, m), 4.41 (1H, brs), 5.54-5.59 (1H, m), 6.88 (1H, d, J=8.4 Hz), 7.14 (1H, d, J=7.2 Hz), 7.49 (1H, t, J=7.8 Hz), 8.40 (3H, brs).

Example 4

Preparation of ((2S,7R)-7-methyl-7,8-dihydro-2H-1, 6,9-trioxa-9a-borabenzo[cd]azulen-2-yl) methanamine

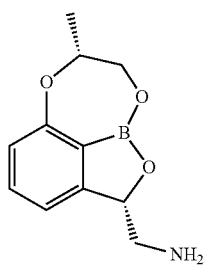 [SMILES: C[C@@H]1COB2O[C@H](CN)c3cccc(c32)O1]

((2S, 7R)-7-methyl-7,8-dihydro-2H-1,6,9-trioxa-9a-borabenzo[cd]azulen-2-yl)methanamine hydrochloride (1 g, 11.0 mmol) prepared by Step 7 of EXAMPLE 3 were dissolved in sodium bicarbonate aqueous solution (80 ml) by neutralization. After removing by extraction with ethyl acetate (100 ml) once, the aqueous layer was extracted with the mixed solvent of methanol (20 ml) and dichloromethane (100 ml) to obtain organic layer. The organic layer was dried over anhydrous sodium sulfate, filtered, and concentrated. The residue was dried under vacuum. The title compound (400 mg) was produced.

$^1$H-NMR (CD$_3$OD, Varian 400 MHz): δ 1.41 (3H, brs), 2.95-2.98 (1H, m), 3.26-3.29 (1H, m), 4.19 (2H, brs), 4.42 (1H, brs), 5.41-5.45 (1H, m), 6.84-6.86 (1H, m), 7.01 (1H, brs), 7.44 (1H, brs).

Example 5

Preparation of ((2S, 7S)-7-methyl-7,8-dihydro-2H-1,6,9-trioxa-9a-borabenzo[cd]azulen-2-yl)methanamine hydrochloride

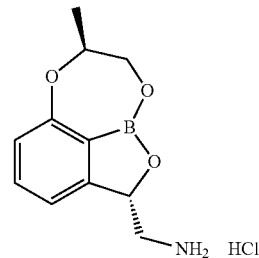 [SMILES: C[C@H]1COB2O[C@H](CN)c3cccc(c32)O1 ; Cl]

[Step 1]Preparation of (R)-1-(benzyloxy)propan-2-yl methanesulfonate

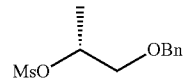

The title compound (27.96 g) was produced according to the substantially same method as described in Step 1 of Example 2, except that starting compound (R)-1-(benzyloxy)propan-2-ol (20 g, 120 mmol) was used instead of starting compound 1-(benzyloxy)propan-2-ol.

$^1$H-NMR (CDCl$_3$, Varian 400 MHz): δ 1.40 (3H, d, J=6.4 Hz), 3.01 (3H, s), 3.52-3.61 (2H, m), 4.55 & 4.57 (2H, ABq, J$_{AB}$=11.8 Hz), 4.88-4.96 (1H, m), 7.26-7.38 (5H, m).

[Step 2]Preparation of (S)-3-((1-(benzyloxy)propan-2-yl)oxy) benzaldehyde

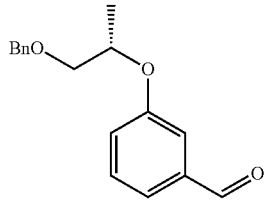

The title compound (19.14 g) was produced according to the substantially same method as described in Step 2 of Example 2, except that starting compound (R)-1-(benzyloxy)propan-2-yl methanesulfonate (27.96 g) was used instead of starting compound 1-(benzyloxy)propan-2-yl methanesulfonate.

$^1$H-NMR (CDCl$_3$, Varian 400 MHz): δ 1.35 (3H, d, J=6.0 Hz), 3.68 (1H, dd, J=10.4, 6.0 Hz), 3.59 (1H, dd, J=10.0, 4.4 Hz), 4.59 (2H, s), 4.63-4.71 (1H, m), 7.18-7.21 (1H, m), 7.28-7.36 (5H, m), 7.40-7.46 (3H, m), 9.95 (1H, s).

[Step 3]Preparation of (S)-1-(3-(((S)-1-(benzyloxy)propan-2-yl)oxy)phenyl)-2-nitroethan-1-ol

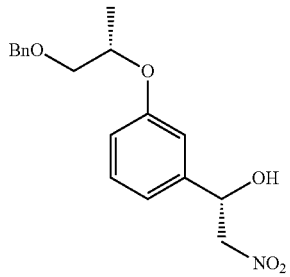

The title compound (20 g) was produced according to the substantially same method as described in Step 3 of Example 2, except that starting compound (S)-3-((1-(benzyloxy)propan-2-yl)oxy) benzaldehyde (19.14 g) was used instead of starting compound 3-((1-(benzyloxy)propan-2-yl)oxy) benzaldehyde.

$^1$H-NMR (CDCl$_3$, Varian 400 MHz): δ 1.33 (3H, d, J=6.4 Hz), 2.90 (1H, brs), 3.57 (1H, dd, J=10.4, 4.4 Hz), 3.66 (1H, dd, J=10.2, 6.2 Hz), 4.45 (1H, dd, J=13.4, 3.0 Hz), 4.51-4.60 (2H, m), 4.58 (2H, s), 5.39 (1H, dd, J=9.6, 2.8 Hz), 6.89-6.99 (3H, m), 7.24-7.38 (6H, m).

[Step 4]Preparation of (S)-2-amino-1-(3-(((S)-1-(benzyloxy)propan-2-yl)oxy)phenyl)ethan-1-ol

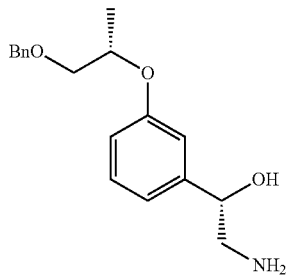 [SMILES: C[C@@H](COCc1ccccc1)Oc1cccc([C@H](O)C[N+](=O)[O-])c1]

The title compound (13 g) was produced according to the substantially same method as described in Step 4 of Example 2, except that starting compound (S)-1-(3-(((S)-1-(benzyloxy)propan-2-yl)oxy)phenyl)-2-nitroethan-1-ol (20 g, 60.4 mmol) was used instead of starting compound (1S)-1-(3-((1-(benzyloxy)propan-2-yl)oxy)phenyl)-2-nitroethan-1-ol.

$^1$H-NMR (CDCl$_3$, Varian 400 MHz): δ 1.31 (3H, d, J=6.0 Hz), 1.88 (3H, brs), 2.77 (1H, dd, J=12.6, 7.8 Hz), 2.96 (1H, dd, J=13.0, 3.8 Hz), 3.54 (1H, dd, J=8.2, 3.0 Hz), 3.65 (1H, dd, J=10.2, 5.8 Hz), 4.57 (2H, s), 4.56-4.62 (2H, m), 6.82 (1H, dd, J=8.2, 1.8 Hz), 6.90 (1H, d, J=7.6 Hz), 6.95-6.96 (1H, m), 7.22 (1H, t, J=7.8 Hz), 7.35-7.25 (5H, m).

[Step 5]Preparation of (S)-1-(3-(((S)-1-(benzyloxy)propan-2-yl)oxy)phenyl)-2-(dibenzylamino)ethan-1-ol hydrochloride

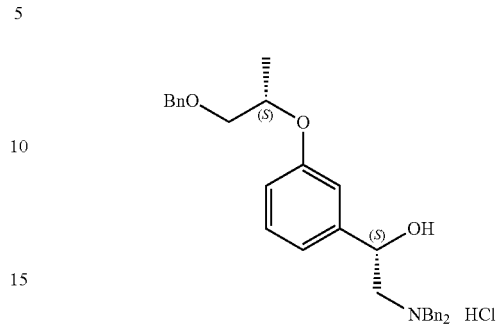

The title compound (10.4 g) was produced according to the substantially same method as described in Step 5 of Example 2, except that starting compound (S)-2-amino-1-(3-(((S)-1-(benzyloxy)propan-2-yl)oxy)phenyl)ethan-1-ol (10.48 g, 34.8 mmol) was used instead of starting compound (1S)-2-amino-1-(3-((1-(benzyloxy)propan-2-yl)oxy)phenyl)ethan-1-ol.

$^1$H-NMR (CDCl$_3$, Varian 400 MHz): δ 1.27 (3H, d, J=6.0 Hz), 2.98-3.03 (1H, m), 3.15-3.21 (1H, m), 3.53 (1H, dd, J=10.2, 4.6 Hz), 3.61 (1H, dd, J=10.4, 6.0 Hz), 4.18 (1H, dd, J=13.4, 6.2 Hz), 4.35 (1H, dd, J=13.2, 5.2 Hz), 4.48-4.55 (3H, m), 4.56 (2H, s), 5.22 (1H, d, J=9.6 Hz), 5.34 (1H, brs), 6.64 (1H, d, J=6.6 Hz), 6.72 (1H, brs), 6.79 (1H, dd, J=8.0, 2.4 Hz), 7.14 (1H, t, J=7.8 Hz), 7.25-7.35 (5H, m), 7.43-7.50 (6H, m), 7.62-7.66 (2H, m), 7.67-7.71 (2H, m), 11.78 (1H, brs).

[Step 6]Preparation of (S)-7-(((S)-1-(benzyloxy)propan-2-yl)oxy)-3-((dibenzylamino)methyl)benzo[c][1,2]oxaborole-1 (3H)-ol

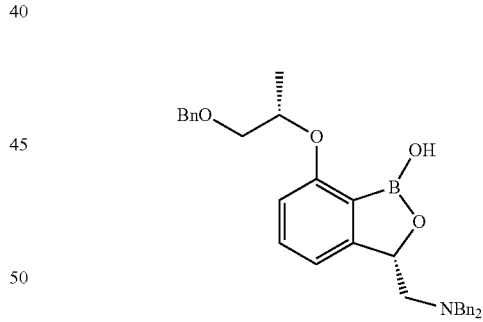

The title compound (700 mg) was produced according to the substantially same method as described in Step 6 of Example 2, except that starting compound (S)-1-(3-(((S)-1-(benzyloxy)propan-2-yl)oxy)phenyl)-2-(dibenzylamino)ethan-1-ol hydrochloride (7 g) was used instead of starting compound (1S)-1-(3-((1-(benzyloxy)propan-2-yl)oxy)phenyl)-2-(dibenzylamino)ethan-1-ol hydrochloride.

$^1$H-NMR (CDCl$_3$, Varian 400 MHz): δ 1.19 (3H, d, J=6.4 Hz), 1.60 (1H, brs), 2.70 (1H, dd, J=14.0, 7.6 Hz), 3.00 (1H, dd, J=14.4, 3.6 Hz), 3.56 (1H, dd, J=10.0, 2.8 Hz), 3.63 (1H, dd, J=10.0, 8.0 Hz), 3.75 (2H, d, J=13.6 Hz) 3.88 (2H, d, J=13.6 Hz), 4.37-4.41 (1H, m), 4.66 & 4.72 (2H, ABq, J$_{AB}$=12.4 Hz), 5.34-5.38 (1H, m), 6.70-6.84 (2H, m), 7.20-7.39 (16H, m).

[Step 7] Preparation of ((2S, 7S)-7-methyl-7,8-di-hydro-2H-1,6,9-trioxa-9a-borabenzo[cd]azulen-2-yl)methanamine hydrochloride

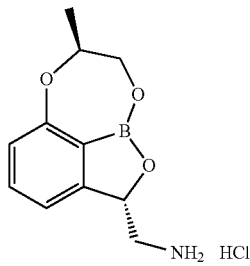 [SMILES: C[C@H]1COB2O[C@H](CN)c3cccc(c32)O1 ; Cl]

The title compound (250 mg) was produced according to the substantially same method as described in Step 7 of Example 2, except that starting compound (S)-7-(((S)-1-(benzyloxy)propan-2-yl)oxy)-3-((dibenzylamino)methyl)benzo[c][1,2]oxaborole-1 (3H)-ol (700 mg) was used instead of starting compound (3S)-7-((1-(benzyloxy)propan-2-yl)oxy)-3-((dibenzylamino)methyl)benzo[c][1,2]oxaborole-1 (3H)-ol.

$^1$H-NMR (DMSO-d6, Varian 400 MHz): δ 1.38 (3H, s), 2.82-2.91 (1H, m), 3.44 (1H, d, J=9.2 Hz), 4.14-4.24 (2H, m), 4.42 (1H, brs), 5.49-5.53 (1H, m), 6.85 (1H, d, J=5.2 Hz), 7.11 (1H, d, J=4.8 Hz), 7.46 (1H, t, J=5.2 Hz), 8.40 (3H, brs).

Chiral property of the title compound was analyzed under the condition

| Chiral analysis condition | |
|---|---|
| System | Dionex |
| Column | φ4.6 × L250 mm, 5 um, Chiralpak IF |
| Flow rate | 1.0 ml/min |
| Wavelength | UV 210 nm |
| Mobile phase | Hexane/Ethanol/Isopropanol/Trifluoroacetic acid/Diethylamine = 900/50/50/3/1 isocratic elution |

Experimental Example 1

Antibacterial Activity In Vitro

The antibacterial activity of the novel derivatives prepared by EXAMPLE 1 to 5 was evaluated in vitro by agar plate dilution method using Mueller-Hinton agar according to the NCCLS (National Committee for Clinical Laboratory Standards. 2000. Methods for dilution antimicrobial susceptibility tests for bacteria that grow aerobically. Approved standard, NCCLS document M7-A5, 5$^{th}$ ed, vol 20, no. 2. National Committee for Clinical Laboratory Standards, Wayne, Pa.). The test strains were clinical isolates from patients in general hospital in Korea from 2010 to 2013. The antibacterial activity was examined against important gram-negative bacteria including carbapenem-resistant *Acinetobacter baumannii* (*A. baumannii*), carbapenem-resistant *Pseudomonas aeruginosa* (*P. aeruginosa*), *Escherichia coli* (*E. coli*), and *Klebsiella pneumonia* (*K. pneumonia*) and was expressed as minimum inhibitory concentrations (MIC, μg/ml) in table 1.

TABLE 1

| test strain | EXAMPLE 1 | EXAMPLE 2 | EXAMPLE 3 | EXAMPLE 4 | EXAMPLE 5 |
|---|---|---|---|---|---|
| E. coli | 2 | 1 | 1 | 1 | 1 |
| K. pneumoniae | 2 | 2 | 2 | 1 | 2 |
| K. oxytoca | 2 | 2 | 1 | 1 | 2 |
| E. cloacae | 2 | 1 | 1 | 1 | 1 |
| E. aerogenes | 4 | 2 | 2 | 1 | 4 |
| C. freundii | 1 | 1 | 1 | 0.5 | 1 |
| M. morganii | 2 | 1 | 1 | 0.5 | 0.5 |
| P. vulgaris | 4 | 2 | 2 | 1 | 2 |
| P. mirabilis | 2 | 2 | 2 | 1 | 2 |
| P. aeruginosa | 32 | 8 | 16 | 8 | 8 |
| A. baumannii | 4 | 2 | 1 | 1 | 4 |
| N. gonorrhoeae | 2 | 1 | 0.5 | 0.5 | 2 |
| S. marcescens | 4 | 4 | 4 | 2 | 4 |

Preparation Example 1

Preparation of (7,8-dihydro-2H-1,6,9-trioxa-9a-borabenzo[cd]azulen-2-yl)methanamine (compound A)

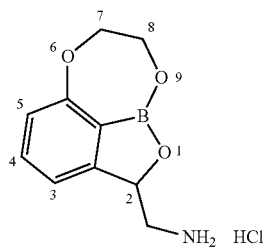 [SMILES: NCC1OB2OCCOc3cccc1c32 ; Cl]

As a control compound, the title compound A 1.7 g which has not substituent at 7$^{th}$, and 8$^{th}$ position, was prepared according to the same method as described in example 24 of WO2013/093615.

$^1$H-NMR (DMSO-d$_6$, Varian 400 MHz): δ 2.87-2.92 (1H, m), 3.42-3.58 (1H, m), 4.15-4.42 (3H, m), 4.62-4.76 (1H, m), 5.45-5.87 (1H, m), 6.92 (1H, d, J=8.0 Hz), 7.15 (1H, d, J=7.2 Hz), 7.50 (1H, dd, J=8.0, 7.6 Hz), 8.26 (3H, brs).

Preparation Example 2

Preparation of (8-methyl-7,8-dihydro-2H-1,6,9-trioxa-9a-borabenzo[cd]azulen-2-yl)methanamine hydrochloride (compound B)

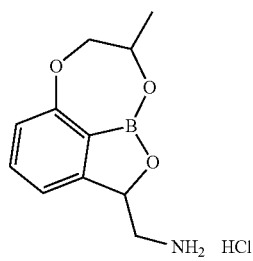 [SMILES: CC1COc2cccc3c2B(O1)OC3CN ; Cl]

The title compound B 45.0 mg was prepared according to the same method as described in example 9 of WO2013/093615.

¹H-NMR (CD₃OD, Varian 400 MHz): δ 1.24-1.36 (3H, m), 2.88-3.00 (1H, m), 3.55-3.64 (1H, m), 4.14-4.23 (1H, m), 4.46-4.57 (2H, m), 5.42-5.48 (1H, m), 6.86-6.96 (1H, m), 7.06 (1H, d, J=6.8 Hz), 7.48 (1H, t, J=7.8 Hz).

Preparation Example 3

Preparation of ((2S,8R)-2-(aminomethyl)-7,8-dihydro-2H-1,6,9-trioxa-9a-borabenzo[cd]azulen-8-yl)methanol hydrochloride (compound C)

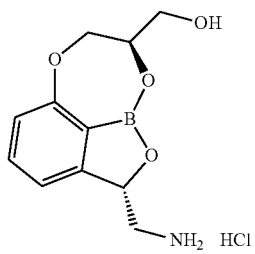 [SMILES: NC[C@H]1OB2O[C@H](CO)COc3cccc1c32 ; Cl]

The title compound C 50 mg was produced according to the same method as described in example 3 of WO2013/093615.

¹H-NMR (DMSO-d₆, Varian 400 MHz): δ 2.90-2.96 (1H, m), 3.52-3.79 (3H, m), 4.03-4.36 (2H, m), 4.72-4.75 (1H, m), 5.01-5.18 (1H, m), 5.49 (1H, brs), 6.93 (1H, d, J=7.6 Hz), 7.20 (1H, d, J=7.2 Hz), 7.50 (1H, t, J=7.8 Hz), 8.12 (3H, brs).

Preparation Example 4

Preparation of (2-(aminomethyl)-7,8-dihydro-2H-1,6,9-trioxa-9a-borabenzo[cd]azulen-7-yl)methanol hydrochloride (compound D)

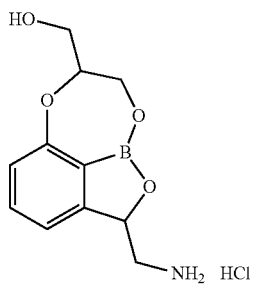 [SMILES: NCC1OB2OCC(CO)Oc3cccc1c32 ; Cl]

The title compound D 12 mg was produced using the same method as described in example 11 of prior art patent WO2013/093615.

¹H-NMR (CD₃OD, Varian 400 MHz): δ 2.97 (1H, dd, J=12.8, 8.8 Hz), 3.52-3.62 (1H, m), 3.72-3.92 (2H, m), 4.18-4.28 (2H, m), 4.42-4.52 (1H, m), 5.46-5.52 (1H, m), 6.95 (1H, d, J=8.4 Hz), 7.05 (1H, d, J=7.2 Hz), 7.49 (1H, t, J=7.8 Hz).

Experimental Example 2

Antibacterial Activity In Vitro

The antibacterial activity of compounds (in Preparation Examples 1 to 4) and meropenem (MEPM, carbapenem-based antibiotics) were examined according to the same method shown as EXPERIMENTAL EXAMPLE 1. The antibacterial activity (MIC, μg/ml) for gram-negative bacteria was summarized in table 2.

TABLE 2

| test strain | compound A | compound B | compound C | compound D | MEPM |
| --- | --- | --- | --- | --- | --- |
| E. coli | 2 | 2 | 2 | 8 | <0.0313 |
| K. pneumoniae | 4 | 4 | 2 | 16 | <0.0313 |
| K. oxytoca | 2 | 2 | 2 | 8 | <0.0313 |
| E. cloacae | 2 | 2 | 2 | 8 | <0.0313 |
| E. aerogenes | 2 | 2 | 4 | 8 | <0.0313 |
| C. freundii | 1 | 1 | 2 | 4 | <0.0313 |
| M. morganii | 2 | 4 | 2 | 8 | 0.125 |
| P. vulgaris | 32 | 16 | 8 | 16 | 0.0625 |
| P. mirabilis | 8 | 8 | 8 | 16 | 0.0625 |
| P. aeruginosa | 8 | 64 | 8 | 64 | 32 |
| A. baumannii | >128 | 8 | 4 | 16 | 32 |

As shown in table 1 and table 2, the MIC values of tricyclic benzoxaborole compounds from the present invention were equivalent to or lower than those of reference compound (compound A, compound B and compound C). The tricyclic benzoxaborole compounds from the present invention represented much more excellent MIC result against the many gram-negative bacteria, compared to the compound D, which is similar to the compound from the present invention, except having hydroxymethyl instead of methyl at 7$^{th}$ carbon.

Moreover, for *Acinetobacter baumannii* which is a typical pathogen in hospital, the compounds from the present invention represented more excellent MIC than compound A, compound B and compound D, as well as MEPM and represented MIC result of equal to or higher than compound C. Particularly, the compounds in EXAMPLEs 2, 3 and 4 represented more excellent MIC than compound C. Because the therapeutical option is limited due to absence of effective antimicrobial agent for infectious disease by carbapenem-resistant *Acinetobacter baumannii*, the tricyclic benzoxaborole compounds from the present invention could be very effective therapeutical agents for bacterial infectious disease.

Experimental Example 3

Antibacterial Activity in Animal Infection Model

Antibacterial activity of the compounds from the present invention was examined in vivo according to the method described in S. Choi et al (*Antimicrob. Agents Chemother* 56 (9) 4713-4717. 2012).

Carbapenem-resistant *Acinetobacter baumannii* BAA-1605 was used as test strain and the test strain was intraperitoneally injected into mouse to cause the systemic infection. After 1 hour of infection, the compounds of EXAMPLEs 1, 2, 3, 5 and the control compounds were administrated orally to the mice. Then, survival rates per dose were observed for 7 days, and the dose needed for the 50 percentage survival rate ($ED_{50}$) was calculated. The result for *Acinetobacter baumannii* BAA-1605 was shown in table 3.

TABLE 3

| Compound | ED$_{50}$ (mg/kg) |
| --- | --- |
| EXAMPLE 1 | 1.749 |
| EXAMPLE 2 | 1.356 |
| EXAMPLE 3 | 0.909 |
| EXAMPLE 5 | 1.356 |
| Compound A | 20> |
| Compound B | 20> |
| Compound C | 9.075 |

As shown in table 3, the oral administration of the compounds from the present invention showed excellent antibacterial effect in the mouse systemic infection model, compared to Compound A, Compound B, and Compound C. ED$_{50}$ values of the compounds obtained in EXAMPLEs 1, 2 and 5 represented 5.18, 6.69 and 6.69 times as low as ED$_{50}$ value of Compound C, respectively. ED$_{50}$ value of EXAMPLE 3 showed 9.98 times as low as ED$_{50}$ value of Compound C.

Based on the experimental results, antibacterial effect of the compounds from the present invention against carbapenem-resistant *Acinetobacter baumannii* in vivo was shown to be much higher than in vitro. Therefore, the compounds from the present invention could be very effective therapeutic agent against antibiotic-resistant bacterial infectious disease.

What is claimed is:

1. A tricyclic benzoxaborole compound represented by Chemical Formula 1, isomer thereof or a pharmaceutically acceptable salt thereof:

[Chemical Formula 1]

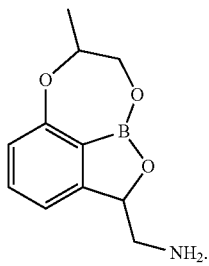

2. The tricyclic benzoxaborole compound, isomer thereof or a pharmaceutically acceptable salt thereof according to claim 1, wherein the isomer is represented by Chemical Formula 2:

[Chemical Formula 2]

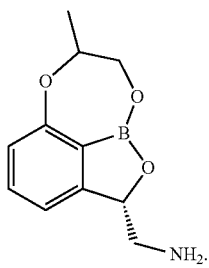

3. The tricyclic benzoxaborole compound, isomer thereof or a pharmaceutically acceptable salt thereof according to claim 1, wherein the isomer is represented by Chemical Formula 3:

[Chemical Formula 3]

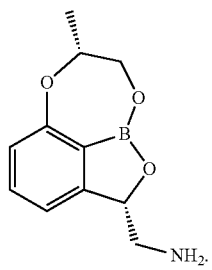

4. The tricyclic benzoxaborole compound, isomer thereof or a pharmaceutically acceptable salt thereof according to claim 1, wherein the compound is selected from the group consisting of:
   1) (7-methyl-7,8-dihydro-2H-1,6,9-trioxa-9a-borabenzo[cd]azulen-2-yl)methanamine hydrochloride;
   2) ((2S)-7-methyl-7,8-dihydro-2H-1,6,9-trioxa-9a-borabenzo[cd]azulen-2-yl)methanamine hydrochloride;
   3) ((2S,7R)-7-methyl-7,8-dihydro-2H-1,6,9-trioxa-9a-borabenzo[cd]azulen-2-yl)methanamine hydrochloride;
   4) ((2S,7R)-7-methyl-7,8-dihydro-2H-1,6,9-trioxa-9a-borabenzo[cd]azulen-2-yl)methanamine; and
   5) ((2S,7S)-7-methyl-7,8-dihydro-2H-1,6,9-trioxa-9a-borabenzo[cd]azulen-2-yl)methanamine hydrochloride.

5. The tricyclic benzoxaborole compound, isomer thereof or a pharmaceutically acceptable salt thereof according to claim 1, wherein the pharmaceutically acceptable salt is formed by acid selected from the group consisting of hydrochloric acid, sulfuric acid, nitric acid, phosphoric acid, hydrobromic acid, hydroiodic acid, tartaric acid, formic acid, citric acid, acetic acid, trichloroacetic acid, trifluoroacetic acid, gluconic acid, benzoic acid, lactic acid, mandelic acid, fumaric acid, maleic acid, salicylic acid, methanesulfonic acid, ethanesulfonic acid, benzenesulfonic acid, and p-toluenesulfonic acid.

6. A method of preparing a tricyclic benzoxaborole compound of Chemical Formula 1, isomer thereof or a pharmaceutically acceptable salt thereof according to claim 1, comprises the steps of:
   coupling a compound of Chemical Formula 4 and a compound of Chemical Formula 5 to prepare a compound of Chemical Formula 6;
   performing a borylation reaction of the compound of Chemical Formula 6 to prepare a compound of Chemical Formula 7 and then performing cyanation to prepare a cyanobenzoxaborole compound of Chemical Formula 8;
   reducing the compound of Chemical Formula 8 to prepare an amino benzoxaborole compound of Chemical Formula 9 by substitution of the cyano group with an amino group;
   introducing a protecting group (PG$_2$) into the amino group of the compound of Chemical Formula 9 to prepare a compound of Chemical Formula 10, performing a condensation reaction of the compound of Chemical Formula 10 to deprotect the protecting group (PG$_1$), and then performing a cyclization reaction to prepare a tricyclic benzoxaborole compound of Chemical Formula 11; and
   deprotecting the amino group (PG$_2$) of the compound of Chemical Formula 11 to prepare a compound of Chemical Formula 1

[Chemical Formula 4]

[Chemical Formula 5]

[Chemical Formula 6]

[Chemical Formula 7]

[Chemical Formula 8]

[Chemical Formula 9]

[Chemical Formula 10]

[Chemical Formula 11]

[Chemical Formula 1]

in Chemical Formulae 4 to 11, $PG_1$ and $PG_2$ are each independently benzyl, t-butyl, Boc (tert-butyloxycarbonyl), pmb (4-methoxybenzyl), Fmoc (Fluorenylmethyloxycarbonyl), Ts (tosylate), MOM (methoxymethyl), THP (tetrahydropyranyl), TBDMS (tert-butyldimethylsilyl), or TBDPS (tert-butyldimethylsilyl), LG is halogen, para-toluenesulfonyl group or a methanesulfonyl group, X is hydrogen, halogen, or trifluoromethanesulfonyl, and Y is hydrogen or $PG_2$.

7. A method of preparing a tricyclic benzoxaborole compound of Chemical Formula 1, isomer thereof or a pharmaceutically acceptable salt thereof according to claim 1 comprises the steps of:

coupling the compound of Chemical Formula 4 and the compound of Chemical Formula 5 to prepare the compound of Chemical Formula 6;

performing a nitration reaction of the compound of Chemical Formula 6 or using a chiral ligand or a chiral catalyst to prepare a compound of Chemical Formula 12 or isomers thereof, reducing the compound of Chemical Formula 12 to prepare the compound of Chemical Formula 13 by substitution of the nitro group with an amino group;

introducing a protecting group (PG$_2$) into the amino group of the compound of Chemical Formula 13 to prepare a compound of Chemical Formula 14, and performing a borylation reaction of the compound of Chemical Formula 14 to prepare the benzoxaborole compound of Chemical Formula 10;

performing a condensation reaction of the compound of Chemical Formula 10 to remove the protecting group (PG$_1$) and then performing a cyclization reaction to prepare a tricyclic benzoxaborole compound of Chemical Formula 11; and deprotecting the amino group of the compound of Chemical Formula 11 to prepare the compound of Chemical Formula 1

[Chemical Formula 4]

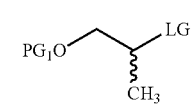

[Chemical Formula 5]

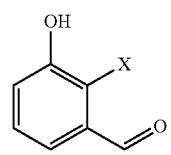

[Chemical Formula 6]

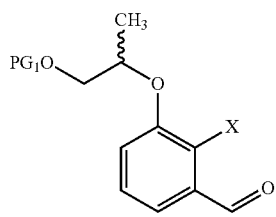

[Chemical Formula 12]

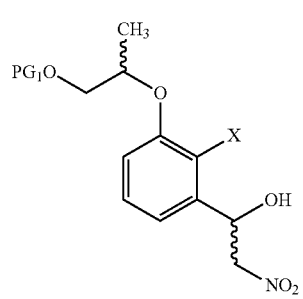

[Chemical Formula 13]

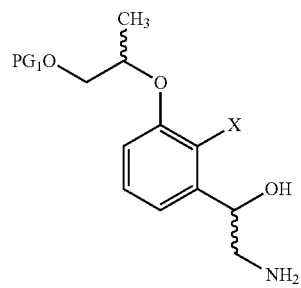

[Chemical Formula 14]

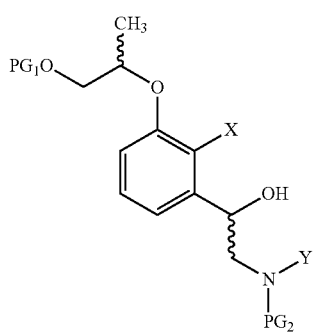

[Chemical Formula 10]

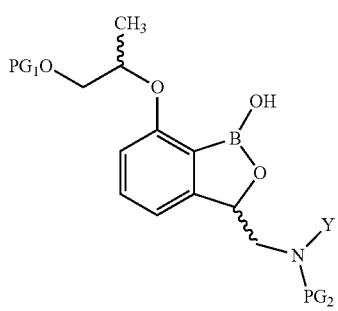

[Chemical Formula 11]

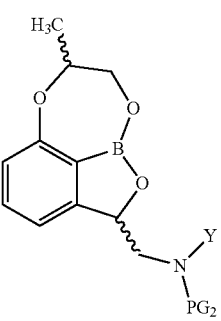

[Chemical Formula 1]

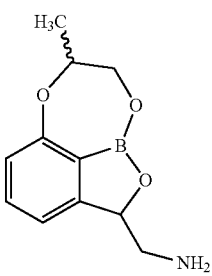

in Chemical Formulae 4 to 6 and 10 to 14, $PG_1$ and $PG_2$ are each independently benzyl, t-butyl, Boc (tert-butyloxycarbonyl), pmb (4-methoxybenzyl), Fmoc (Fluorenylmethyloxycarbonyl), Ts (tosylate), MOM (methoxymethyl), THP (tetrahydropyranyl), TBDMS (tert-butyldimethylsilyl), or TBDPS (tert-butyldimethylsilyl), LG is halogen, para-toluenesulfonyl group or a methanesulfonyl group, X is hydrogen, halogen, or trifluoromethanesulfonyl, and Y is hydrogen or $PG_2$.

8. The method according to claim 6, wherein the borylation reaction is performed using bis (pinacolato)diboron or 2-isopropoxy-4,4,5,5-tetramethyl-1,3,2-dioxaborolan.

9. A pharmaceutical composition with an antibiotic activity to Gram-negative bacterium, comprises the compound, isomer thereof or a pharmaceutically acceptable salt thereof according to claim 1, as an active ingredient.

10. The pharmaceutical composition according to claim 9, wherein the Gram-negative bacterium is a multidrug-resistant Gram-negative bacterium.

11. The pharmaceutical composition according to claim 10, wherein the Gram-negative bacterium is carbapenem-resistant Gram-negative bacterium.

12. The pharmaceutical composition according to claim 9, wherein the Gram-negative bacterium is *A.baumannii, C.freundii, E.coli, E.cloacae, E.aerogenes, K.pneumoniae, K.oxytoca, M.morganii, P.aeruginosa P.vulgaris, P.mirabilis, N. gonorrhoeae* or *S.marcescens*.

13. The pharmaceutical composition according to claim 12, wherein the Gram-negative bacterium is a multidrug-resistant Gram-negative bacterium.

14. The pharmaceutical composition according to claim 13, wherein the Gram-negative bacterium is carbapenem-resistant Gram-negative bacterium.

15. The method according to claim 7, wherein the borylation reaction is performed using bis (pinacolato)diboron or 2-isopropoxy-4,4,5,5-tetramethyl-1,3,2-dioxaborolan.

16. A method of treating Gram-negative bacterial infection in a mammal, which comprises administering to said mammal a composition comprising a therapeutically or prophylactically effective amount of a tricyclic benzoxaborole compound represented by Chemical Formula 1, isomer thereof, or a pharmaceutically acceptable salt thereof:

[Chemical Formula 1]

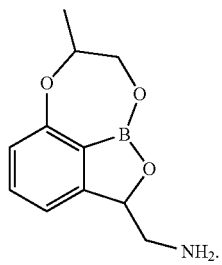

* * * * *